(12) United States Patent
Hansen et al.

(10) Patent No.: US 10,238,742 B2
(45) Date of Patent: Mar. 26, 2019

(54) CELL PENETRATING NUCLEOLYTIC ANTIBODY BASED CANCER THERAPY

(71) Applicants: Yale University, New Haven, CT (US); The United States of America as represented by the Department of Veteran Affairs, Washington, DC (US)

(72) Inventors: James E. Hansen, Guilford, CT (US); Richard H. Weisbart, Los Angeles, CA (US); Philip W. Noble, New Haven, CT (US)

(73) Assignees: Yale University, New Haven, CT (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/750,683

(22) Filed: Jun. 25, 2015

(65) Prior Publication Data

US 2015/0376279 A1 Dec. 31, 2015

Related U.S. Application Data

(60) Provisional application No. 62/016,960, filed on Jun. 25, 2014.

(51) Int. Cl.
*A61K 45/06* (2006.01)
*C07K 16/44* (2006.01)

(52) U.S. Cl.
CPC .............. *A61K 45/06* (2013.01); *C07K 16/44* (2013.01); *C07K 2317/73* (2013.01); *C07K 2317/77* (2013.01)

(58) Field of Classification Search
CPC .... A61K 45/06; C07K 16/44; C07K 2317/73; C07K 2317/77
USPC .......................................... 424/133.1, 178.1
See application file for complete search history.

(56) References Cited

U.S. PATENT DOCUMENTS

| | | | |
|---|---|---|---|
| 4,812,397 A | 3/1989 | Weisbart | |
| 5,780,033 A | 7/1998 | Torchilin | |
| 7,189,396 B1 | 3/2007 | Weisbart | |
| 9,701,740 B2 | 7/2017 | Hansen et al. | |
| 2002/0090608 A1 | 7/2002 | Palese | |
| 2003/0083305 A1 | 5/2003 | Palese | |
| 2003/0109475 A1 | 6/2003 | Debs | |
| 2004/0033235 A1 | 2/2004 | Bolognesi | |
| 2004/0052820 A1 | 3/2004 | Bolognesi | |
| 2005/0003343 A1 | 1/2005 | Palese | |
| 2005/0221400 A1 | 10/2005 | Gudas | |
| 2005/0256073 A1 | 11/2005 | Lipford | |
| 2006/0110740 A1 | 5/2006 | Hurwitz | |
| 2006/0216701 A1 | 9/2006 | Palese | |
| 2006/0263367 A1 | 11/2006 | Fey | |
| 2008/0004561 A1 | 1/2008 | Genkin | |
| 2008/0292618 A1 | 11/2008 | Weisbart | |
| 2009/0028901 A1 | 1/2009 | Palese | |
| 2009/0186337 A1 | 7/2009 | Eleouet | |
| 2009/0186802 A1* | 7/2009 | Alluis | A61K 31/74 514/1.1 |
| 2010/0143358 A1 | 6/2010 | Weisbart | |
| 2010/0196993 A1 | 8/2010 | Nishimura | |
| 2010/0311171 A1 | 12/2010 | Nakanishi | |
| 2011/0300164 A1 | 12/2011 | Lipford | |
| 2012/0010124 A9* | 1/2012 | Alluis | A61K 31/74 514/1.3 |
| 2012/0214240 A1 | 8/2012 | Nakanishi | |
| 2013/0137644 A1* | 5/2013 | Alluis | A61K 31/74 514/20.9 |
| 2013/0266570 A1 | 10/2013 | Weisbart | |
| 2014/0050723 A1 | 2/2014 | Hansen | |
| 2014/0234309 A1 | 8/2014 | Nishimura | |
| 2015/0376279 A1 | 12/2015 | Hansen | |
| 2016/0235859 A1* | 8/2016 | Weisbart | A61K 47/48538 |
| 2017/0073429 A1 | 3/2017 | Hansen | |
| 2017/0291961 A1 | 10/2017 | Hansen | |

FOREIGN PATENT DOCUMENTS

| | | |
|---|---|---|
| WO | 9732602 | 9/1997 |
| WO | WO 2004/003019 | * 6/2004 |
| WO | 2008091911 | 7/2008 |
| WO | 2009134027 | 11/2009 |
| WO | 2012145125 | 10/2012 |
| WO | 2015106290 | 7/2015 |
| WO | 2015134607 | 9/2015 |
| WO | 2016033321 | 3/2016 |
| WO | 2016033324 | 3/2016 |

OTHER PUBLICATIONS

Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Brummell et al. (Biochemistry 32:1180-1187 (1993)).*
Kobayashi et al. (Protein Engineering 12:879-844 (1999)).*
Burks et al. (PNAS 94:412-417 (1997)).*

(Continued)

*Primary Examiner* — Lynn A Bristol

(74) *Attorney, Agent, or Firm* — Pabst Patent Group LLP

(57) ABSTRACT

Cancer cells with defects in DNA repair are highly susceptible to DNA-damaging agents, but delivery of therapeutic agents into cell nuclei can be challenging. A sub-set of autoantibodies having nucleolytic activity are capable of nuclear penetration. These antibodies can be used as therapeutic agents targeted towards DNA repair-deficient malignancies.

12 Claims, 4 Drawing Sheets

Specification includes a Sequence Listing.

(56) References Cited

OTHER PUBLICATIONS

Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Ford (Sci Transl Med. (Oct. 24, 2012); 4(157):157-160).*
Achuthan, et al., "Drug-induced senescence generates chemoresistant stemlike cells with low reactive oxygen species", J. Biol. Chem., 286:37813-29 (2011).
Adjei, "Blocking oncogenic Ras signaling for cancer therapy", J Natl Cancer Inst., 93(14):1062-74 (2001).
Alarcon-Segovia, "Antinuclear antibodies: to penetrate or not to penetrate, that was the question", Lupus, 10:315-8 (2001).
American Cancer Society, Cancer Facts & Figures, pp. 1-70 (2014).
Arnaudeau, et al., "DNA double-strand breaks associated with replication forks are predominantly repaired by homologous recombination involving an exchange mechanism in mammalian cells", J Mol Biol, 307:1235-45 (2001).
Bernatsky, et al., Breast, ovarian, and endometrial malignancies in systemic lupus erythematosus: a meta-analysis Br. J. Cancer 104:1478-81(2011a).
Bernatsky, et al., "Cancer risk in systemic lupus: an updated international multi-centre cohort study", J. Autoimmun. 42:130-5 (2013).
Bernatsky, et al., "Decreased breast cancer risk in systemic lupus erythematosus: the search for a genetic basis continues", Lupus, 21:896-9 (2008b).
Bernatsky, et al., "Prostate cancer in systemic lupus erythematosus", Int. J. Cancer, 129: 2966-9 (2011b).
Bernatsky, et al., "The relationship between cancer and medication exposures in systemic lupus erythaematosus: a case-cohort study", Ann. Rheum. Dis. 67:74-9 (2008).
Bindra, et al., "Down-regulation of Rad51 and decreased homologous recombination in hypoxic cancer cells", Mol. Cell. Biol., 24(19):8504-18 (2004).
Bryant, et al., "Specific killing of BRCA2-deficient tumours with inhibitors of poly (ADP-ribose) polymerase", Nature, 434:913-7 (2005).
Chan, et al., "Targeting cancer with a cell-penetrating anti-DNA antibody", J Investigative Med., 60(1):148 (2012).
Chi, et al., "Roles of ATP binding and ATP hydrolysis in human Rad51 recombinase function", DNA Repair (Amst) 5:381-91 (2006).
Colburn, et al., "Anti-guanosine antibodies in murine and human lupus have the internal image of G-binding proteins", J Rheumatol., 30(5):993-7 (2003).
Colburn, et al., "Serum antibodies as a marker for SLE disease activity and pathogen potential", Clinica Chimica Acta, 370:9-16 (2006).
Derossi, et al., "The third helix of the Antennapedia homeodomain translocates through biological membranes", J. Biol. Chem. 269(14):10444-50 (1994).
Dray , et al., "Molecular basis for enhancement of the meiotic DMC1 recombinase by RAD51 associated protein 1 (RAD51AP1)", PNAS, 108:3560-5 (2011).
Farmer, et al., "Targeting the DNA repair defect in BRCA mutant cells as a therapeutic strategy", Nature 434:917-21 (2005).
Feng, et al., "Rad52 inactivation is synthetically lethal with BRCA2 deficiency" PNAS, 108:686-91 (2011).
Frankel and Pabo, "Cellular uptake of the tat protein from human immunodeficiency virus", Cell, 55(6):1189-93 (1988).
Gu, et al. "Genetic determinants of autoimmune disease abd coronary vasculitis in the MRL-lpr/lpr mouse model of systemic lupus erythematosus", J Immunol., 161:6999-7006 (1998).
Gysin, et al., "Therapeutic strategies for targeting ras proteins", Genes Cancer, 2(3):359-72 (2011).

Hansen, et al., "Antibody-mediated Hsp70 protein therapy", Brain Res., 1088(1):187-96 (2006).
Hansen, et al., "Antibody-mediated p53 protein therapy prevents liver metastasis in vivo", Cancer Res., 67(4):1769-74 (2007a).
Hansen, et al., "Intranuclear protein transduction through a nucleoside salvage pathway", J Biol Chem., 282:20790-3 (2007b).
Hansen, et al., "Targeting cancer with a lupus autoantibody", Sci Translational Med., 4(157):157ra142 (2012).
Hoeijmakers, "DNA damage, aging, and cancer", N. Engl. J. Med. 361:1475-85 (2009).
Itoh, et al., "Diagnostic use of anti-modified nucleoside monoclonal antibody" Tohoku J Exp Med., 168(2):329-31 (1992).
Jordan, et al., Mechanism of mitotic block and inhibition of cell proliferation by taxol at low concentrations, PNAS, 90:9552-6 (1993).
Kabouridis, "Biological applications of protein transduction technology", Trends in Biotechnol., (11):498-503 (2003).
Kaelin, Jr., et al., "The concept of synthetic lethality in the context of anticancer therapy", Nat Rev Cancer, 5:689-98 (2005).
Lau, et al., "Suppression of HIV-1 infection by a small molecule inhibitor of the ATM kinase", Nat Cell Biol, 7(5): 493-500 (2005).
Lee, et al., "Gene silencing by cell-penetrating, sequence-selective and nucleic-acid hydrolyzing", Nucleic Acid Res., pp. 1-14 (2009).
Li, et al., "Homologous recombination in DNA repair and DNA damage tolerance", Cell Res., 18:99-113 (2008).
List, et al., "Advances in the understanding of the Fc gamma receptors-mediated autoantibodies uptake", Clin Exp Med 11:1-10 (2011).
Moynahan, et al., "BRCA2 is required for homology-directed repair of chromosomal breaks", Mol Cell, 7:263-72 (2001).
Rahman and Isenberg, "Systemic lupus erythematosus", N. Engl. J. Med. 358:929-39 (2008).
Sakai, et al., "Functional restoration of BRCA2 protein by secondary BRCA2 mutations in BRCA2-mutated ovarian carcinoma", Cancer Res., 69:6381-6 (2009).
Spertini, et al., "Idiotypic vaccination with a murine anti-dsDNA antibody: phase I study in patients with nonactive systemic lupus erythematosus with nephritis", J Rheumatol 269120:2602-8 (1999).
Stachelek, et al., "Potentiation of temozolomide cytotoxicity by inhibition of DNA polymerase beta is accentuated by BRCA2 mutation", Cancer Re.,s 70:409-17 (2010).
Sung, et al., "DNA strand exchange mediated by a RAD51-ssDNA nucleoprotein filament with polarity opposite to that of RecA", Cell, 82:453-61 (1995).
Sung, et al., "Rad51 recombinase and recombination mediators", J Biol Chem., 278:42729-32 (2003).
Sung, "Catalysis of ATP-dependent homologous DNA pairing and strand exchange by yeast RAD51 protein", Science 265:1241-3 (1994).
te Poele, et al., "DNA damage is able to induce senescence in tumor cells in vitro and in vivo", Cancer Res. 62:1876-1883 (2002).
Tewey, et al., "Adriamycin-induced DNA damage mediated by mammalian DNA topoisomerase II", Science 226:466-8 (1984).
Weisbart, et al., "A cell-penetrating bispecific antibody for therapeutic regulation of intracellular targets", Mol Cancer Ther., 11:2169 (2012).
Weisbart, et al., "A conserved anti-DNA antibody idiotype associated with nephritis in murine and human systemic lupus erythematosus", J Immunol 144 (7):2653-8 (1990).
Weisbart, et al., "Novel protein transfection of primary rat cortical neurons using an antibody that penetrates living cells", J Immunol., 164: 6020-6 (2000).
Xu, et al., "Dual DNA unwinding activities of the Rothmund-Thomson syndrome protein, RECQ4", EMBO J 28:568-77 (2009b).
Xu, et al., "MCM10 mediates RECQ4 association with MCM2-7 helicase complex during DNA replication", EMBO J., 28:3005-14 (2009a).
Yoder, et al., "The base excision repair pathway is required for efficient lentivirus integration", PLoS One, 6(3) e17862 (2011).
Young, et al., "Abstract 654: targeting K-ras cancer cells with a lupus anti-guanosine antibody", Cancer Res., 74(19 Supp):654 (2014).
Zack, et al., "DNA mimics a self-protein that may be a target for some anti-DNA antibodies in systemic lupus erythematosus", J. Immunol. 154(4):1987-94 (1995).

(56) References Cited

OTHER PUBLICATIONS

Zack, et al., "Mechanisms of cellular penetration and nuclear localization of an anti-double strand DNA autoantibody", J Immunol., 157:2082-8 (1996).
Zhan, et al., "Recombinant Fv-Hsp70 protein mediates neuroprotection after focal cerebral ischemia in rats", Stroke, 41(3):538-43 (2010).
ATCC CCl-86 Raji, Homo sapiens lymphoblast Burkitt s lymph, http://www.aroc.org/Products/ALL/CCL-86.aspx?&p=1&rel=characteristics, 1 page, retrieved from the internet Jul. 10, 2015.
ATCC CRL-1651 COS-7, Cercopithecus aethiops kidney, http://www.aroc.org/Products/ALL/CRL1651,aspx 1 page, retrieved from the internet Jul. 12, 2015.
Barka, et al., "Transduction of TAT-HA—galactosidase Fusion Protein into Salivary Gland-derived Cells and Organ Cultures of the Developing Gland, and into RatSubmandibular Gland In Vivo", Histochem Cytochem, 48(11):1453-60 (2000).
Bassi, et al., "Nuclear PTEN controls DNA repair and sensitivity to genotoxic stress", Science, 341:395-9 (2013).
Bitzer, et al., "Sendai virus vectors as an emerging negative-strand RNA viral vector system", J Gene Med., 5(7):543-53 (2003).
CELLDEX, "CDX-011 Clinical program", http://www.celldextherapeutics.com/wt/page/cds_011_breast?CMP=KNC-3GS620403736., retrieved from the interned Mar. 31, 2011.
Chothia and Lesk, "Canonical structures for the hypervariable regions of immunoglobulins", J Mol. Biol., 196:901-17 (1987).
Cleaver, et al., "Phosphorylated H2Ax is not an unambiguous marker for DNSA double-strand breaks", Cell Cycle, 10:3223-4 (2011).
Coffin, HIV population dynamics in vivo: implications for genetic variation, pathogenesis, and therapy, Science, 267:483-9 (1995).
Collingridge, et al., "Pentoxifylline improves the oxygenation and radiarion response of BA 1112 rat rhabdomyosarcomas and EMT6 mouse mammary carcinomas", Int J Cancer, 90(5):256-64 (2000).
Collins, et al., "Viral vectors in cancer immunotherapy: which vector for which strategy", Curr Gene Ther., 8(2):66-78 (2008).
Cuesta, et al., "Multivalent antibodies: when design surpasses evolution", Trends in Biotechnol., 28(7):355-62 (2010).
Dean, et al, "Current advances in the translation of cascular tissue engineering to the treatment of pediatric congenital heart disease", Yale J Biol Med, 85:229-38 (2012).
Deyev, et al., "Multivalemcy: the hallmark of antibodies used for optimization of tumor targeting by design", Bioesseays, 30(9):904-18 (2008).
Dimri, et al., "A biomarker that identifies senescent human cells in culture and in aging skin in vivo", PNAS, 92(20):9363-7 (1995).
Florica, The role of topotecan in the treatment of advanced cervical cancer, Gynecol Oncol., 90:S16-21 (2003).
Foroutan, et al., Molecular cytogenetic analysis of chemoresistant non-Hodgkin's lymphoma patients with p53 abnormalities using fluorescence in situ hybridisation and comparative genomic hybridisation, Arch Iran Med., 14 (5):321-6 (2011).
Fusaki, et al., "Efficient induction of transgene-free human pluripotent stem cells using a vector based on Sendai virus, an RNA virus that does not integrate into the host genome", Proc Jpn Acad Ser., B85:348-62 (2009).
Genbank, Accession No. L16981.1, "Mouse Ig rearranged L-chain gene, partial cds",1 page, First available May 2, 1995, accessed Mar. 28, 2016.
Genbank, Accession No. AAA65679.1, "immunoglobulin heavy chain, partial [Mus musculusj]", 2 pages, First available May 2, 1995, accessed Mar. 28, 2016.
Genbank, Accession No. AAA65681.1, "immunoglobulin light chain, partial [Mus musculus]", 2 pages, First available May 2, 1995, accessed Mar. 28, 2016.
Genbank, Accession No. AAA65682.1, This CDS feature is included to show the translation of the of the corresponding V_region. Presently translation qualifiers on V_regions features are illegal, partial [Mus musculus], 1 page, First available May 2, 1995, accesssed Jun. 21, 2016.

Grudzien-Nogalska, et al., "Phosphorothioate cap analogs stabilize mRNA and increase translational efficiency in mammalian cells", RNA, 13(10):1745-55 (2007).
Gruhne, et al., Three Epstein-Barr virus latency proteins independently promote genomic instability by inducing DNA damage, inhibiting DNA repair and inactivating cell cycle checkpoints, Oncogene, 28:3997-4008 (2009).
Hacein-Bey-Abina, et al., "LMO-2associated clonal T cell proliferation in two patients after gene therapy for SCID-X1", Science, 302(5644):415-9 (2003).
Halazonetis, et al., "An oncogene-induced DNA damage model for cancer development", Science, 319(5868):1352-5 (2008).
Hansen, et al. "antibody mediated transduction of therapeutic proteins into living cells", Scientific world, 5(9):782-8 (2005).
Harrington, et al., "VX-680, a ptent and selective small-molecule inhibitor of aurora kinases suppresses tumor growth in vivo", Nat Med., 10:262-7 (2004).
Hayflick, et al., "The limited in vitro lifetime of human diploid cell strains", Exp Cell Res., 37:614-36 (1965).
Ho, et al., "Synthetic protein transduction domains: enhanced transduction potential in vitro and in vivo", Cancer Res., 61(2):474-7 (2001).
Holtkemp, et al., "Modification of antigen-encoding RNA increases stability, translational efficacy, and T-cell stimulatory capacity of dendritic cells", Blood, 108(13):4009-17 (2006).
Hucl, et al., "A syngeneic variance library for functional annotation of human variation: application to BRCA2", Cancer Res., 68:5023-30 (2008).
Jain, et al., "Engineering antibodies for clinical applications", Trends in Biotechnol, 25(7):307-16 (2007).
Jang, et al., "Drug delivery and transport to solid tumors", Phar. Res., 20:1337-50 (2003).
Kabat, et al., "Sequences of proteins of Immunological Interest", 5 Ed Public Health service, National Institutes of Health, Bethesda Md. (1991).
Kane, et al., "Methylation of the hMLH1 promoter correlates with lack of expression of hMLH1 in sporadic colon tumors and mismatch repair-defective human tumor cell lines", Cancer Rev., 57:808-11 (1997).
Kay, "State of the art gene-based therapies: the road ahead", Nature Rev Genetics, 12(5):316-28 (2011).
Kellner, et al., "Boosting ADCC and CDC activity by Fc engineering and evaluation of antibody effector functions", Methods, 65:105-13 (2014).
Kozyr, et al., Anti-DNA autoantibodies reveal toxicity to tumor cell lines, Immunol Lttr., 80:41-7 (2002).
Levitt, et al., "PTEN-induction in U251 glioma cells decreases the expression of insulin-like growth factor binding protein-2", Biochem Biophys Res Comm., 336:1056-61 (2005).
Lewitzky, et al., "Reprogramming somatic cells towards pluripotency by defined factors", Curr Opin Biotechnol., 18:467-73 (2007).
Li, et al., "PTEN, a putative protein tyrosine phosphatase gene mutated in human brain, breast, and prostate cancer", Science, 275:1943-7 (1997).
Liao, et al., "The comet assay: a sensitive method for detecting DNA damage in individual cells", Methods, 48(1):46-53 (2009).
Liu, et al., "A novel bivalent single-chain variable fragment (scFV) inhibits the action of tumor necrosis factor [alpha]", Biotechnol App Biochem., 50(4):173-9 (2008).
Maeda, et al., "Tumor vascular permeability and the EPR effect in macromolecular therapeutics: a review", J Controlled Release, 65:271-84 (2000).
McCabe, et al., "BRCA2-deficient CAPAN-1 cells are extremely sensitive to the inhibition of Poly (ADP-Ribose) polymerase: an issue of potency", Cancer Biology Therapy, 4:934-6 (2005).
McEllin, et al., "PTEN loss compromises homologous recombination repair in astrocytes: implications for glioblastoma therapy with temozolomide or poly(ADP-ribose) polymerase inhibitors", Cancer Res., 70:5457-64 (2010).
Muller, et al., "TransMabs: cell-penetrating antibodies, the next generation", Exp Opin Biol Ther., 5(2):1-5 (2005).

(56) References Cited

OTHER PUBLICATIONS

Nakanishi, et al., "Development of sendai virus vectors and their potential applications in gene therapy and regenerative medicine", Curr Gene Ther., 12(5):410-6 (2012).
Noble, et al., "A cell-penetrating nucleoltyic lupus autoantibody damages DNA and is toxic to BRCA2-deficient cancer cells" poster presented at the Proceedings: AACR Annual Meeting Apr. 5-9, 2014, San Diego, CA (2014).
Noble, et al., "A cell-penetrating nucleolytic lupus autoantibody damages DNA and is toxic to BRCA2-deficient cancer cells", Abstract 4220, Cancer Res, 74:4220 (2014).
Noble, et al., Optimizing a lupus autoantibody for targeted cancer therapy , Cancer Res., 75(11):2285-91 (2015).
Okita, et al., "Induction of pluripotency by defined factors", Exp Cell Res., 316(16):2565-70 (2010).
PARP Inhibitor, http://www.parp-inhibitors.com, retrieved from the Internet Mar. 31, 2011.
Pavlovic, et al., Pathogenic and epiphenomenal anti-DNA antibodies in SLE , Autoimmime Diseases, 2010:462841 1-18 (2010).
Porter, et al., "Chimeric antigen receptor-midified T cells in chronic lymphoid leukemia", NEJM, 365(8):725-33 (2011).
Puc, et al., "PTEN loss inhibits CHK1 to cause double stranded-DNA breaks in cells", Cell Cycle, 4:927-9 (2005).
Rabinovich, et al., "Chimeric receptor mRNA transfection as a tool to generate antineoplastic lymphocytes", Human Gene Therapy, 20(1):51-61 (2009).
Rabinovich, et al. "Synthetic messenger RNA as a tool for gene therapy", Hum Gene Ther., 17(10):1027-35 (2006).
Ratnam, et al., "Current development of clinical inhibitors of poly(ADP-ribose) polymerase in oncology", Clin Cancer Res., 13(5):1383-8 (2007).
Ritter, et al., "Gene therapy in transplantation: Toward clinical trials", Curr Opin Mol Ther., 11(5):504-12 (2009).
Scott, et al., "Antibody therapy of cancer", Nature Reviews Cancer, 12:278-87 (2012).
Sliwinska, et al., Induction of senescence with doxorubicin leads to increased genomic instability of HCT116 cells , Mech. Ageing Dev., 130:24-32 (2009).
Stanulis-Praeger, et al., "Cellular senescence revisited: a review", Mech Ageing Derv, 38:1-48 (1987).
Steck, et al., "Identification of a candidate tumour suppressor gene, MMAC1, at chromosome 10q23.3 that is mutated in multiple advanced cancers", Nat Genet., 15:356-62 (1997).
Stepinski, et al., "Synthesis and properties of mRNA\s containing the novel "anti-reverse" cap analogs 7-methyl(3\-O-methyl)GppppG and 7-methyl (3\-deoxy)GppppG", RNA 7 (10:1486-95 (2001).
Vlietstra, et al., "Frequent inactivation of PTEN in prostate cancer cell lines and xenografts", Cancer Res., 58:2720-3 (1998).
Wadia and Stan, "Transducible TAT-HA fusogenic peptide enhances escape of TAT-fusion proteins after lipid raft micropinocytosis", Nat Med., 10(3):310-5 (2004).
Walpita, et al., "Reverse genetics of negative-stranded RNA viruses: a global perspective", FEMS Microbial. Lett., 244(1):9-18 (2005).
Wang, Mutagenesis in mammalian cells induced by triple helix formation and transcription-coupled repair, Science, 271(5250):802-5 (1996).
Warren, et al., "Highly efficient reprogramming to pluripotency and directed differentiation of human cells with synthetic modified mRNA", Cell Stem Cell, 7(5):618-30 (2010).
Weisbart, et al., "An autoantibody is modified for use as a delivery system to target the cell nucleus: therapeutic implications", J Autoimmun., 11:539-46 (1998).
Weisbart, et al., "Antibody-mediated transduction of p53 selectively kills cancer cells", Int J Oncol., 25:1867-73 (2004).
Weisbart, et al., Nuclear delivery of p53 C-terminal peptides into cancer cells using scFv fragments of a monoclonal antibody that penetrates living cells , Cancer Lttrs., 195:211-19 (2003).
Wender, et al., "The design, synthesis, and evaluation of molecules that enable or enhance cellular uptake: peptoid molecular transporters", PNAS, 97(24):13003-8 (2000).

Yee, et al., "The fine specificity of IgG antiguanosine antibodies in systemic lupus erythematosus", Clin Immunol Immunopathol., 36(2):161-7 (1985).
Yoshizaki, et al., "Naked sendai virus vector lacking all of the envelope-related genes: reduced cytopathogenicity and immunogenicity", J Gene Med., 8(9):1151-9 (2006).
Zack, et al., Novel structural features of aautoantibodies in murine lupis: A possible superantigen binding site , Immonol Cell Biol., 72:513-20 (1994).
Kim, et al., "Heavy and light chain variable single domains of an anti-DNA binding antibody hydrolyze both double- and single-stranded DNAs without sequence specificity", J Biological Chem., 281(22):15287-95 (2006).
Lee, et al., "Cell-penetrating autoantibody induces caspase-mediated apoptosis through catalytic hydrolysis of DNA", Bioorg Med Chem., 15:2016-23 (2007).
Stone, et al., "Neoadjuvant chemotherapy and liver transplantation for hepatocellular carcinoma: a pilot study in 20 patients", Gastroenterology, 104(1):196-202 (1993) Abstract Only.
Weisbart, et al.,"Construction and expression of a bispecific single-chain antibody that penetrates mutant p53 colon cancer cells and binds p53", Int J Oncology, 25:1113-8 (2004).
Berglund, et al., "The epitope space of the human proteome", Protein Sci., 17:606-13 (2008).
Corada, et al., "Monoclonal antibodies directed to different regions of vascular endothelial cadherin extracellular domain affect adhesion and clustering of the protein and modulate endothelial permeability", Blood, 97(6):1679-84 (2001).
Eivazova, et al., "Specificity and binding kinetics of murine lupus anti-DNA monoclonal antibodies implicate different stimuli for their production", Immunology, 101:371-7 (2000).
Kulkarin-Kale, et al., "CEP: a conformational epitope prediction server", Nucleic Acids Res., 33:W168-W171 (2005).
Padlan, "X-ray crystallography of anti-bodies", Adv Protein Chem., 49:57-133 (1996).
Rivadeneyra-Espinoza, et al., "Cell-penetrating anti-native DNA antibodies trigger apoptosis through both the neglect and programmed pathways", J Auto Immunity, 26:52-6 (2006).
Tzartos, et al., "Epitope mapping by antibody completion", Methods Molecular Biol., 66:55-66 (1996).
U.S. Appl. No. 15/615,416, Hansen.
Ahmed, et al., "Extracellular renal guanosine cyclic 3'5'-monophosphate modulates nitric oxide and pressure-induced natriuresis." *Hypertension*, 50:958-63 (2007).
Andersen, et al.,"Identification of heme oxygenase-1-specific regulatory CD8+ T cells in cancer patients," *Journal of Investigative Medicine* (2009).
Apte, et al., "Doxorubicin in TAT peptide-modified multifunctional immunoliposomes demonstrates increased activity against both drug-sensitive and drug-resistant ovarian cancer models" *Cancer Biology & Therapy*, 15:1, 69-80 (2013).
Chen, et al., "A lupus anti-DNA autoantibody mediates autocatalytic, targeted delivery of nanoparticles to tumors" *Oncotarget*, 7(37): 59965-59975 (2016).
Colburn, et al., "Circulating antibodies to guanosine in systemic lupus erythematosus: correlation with nephritis and polyserositis by acute and longitudinal analyses." *Lupus*, 10:410-7 (2001).
Demers, et al., "Cancers predispose neutrophils to release extracellular DNA traps that contribute to cancer-associated thrombosis," *Proc Natl Acad Sci USA*, 109(32):13076-13081 (2012).
Deutsch, et al., "Guanosine possesses specific modulatory effects on NMDA receptor-mediated neurotransmission in intact mice," *Eur Neuropsychopharmacol*, 18:299-302 (2008).
Dowdy, et al., "Cationic PTD/CPP-mediated macromolecular delivery: charging into the cell," *Expert Opin Drug Deliv*, 12:1627-36(2015).
Elbayoumi, et al., "Antinucleosome antibody-modified liposomes and lipid-core micelles for tumor-targeted delivery of therapeutic and diagnostic agents," *Journal of Liposome Research*, 17:1, 1-14 (2007).
Fujita, et al., "Brain tumor tandem targeting using a combination of monoclonal antibodies attached to biopoly(beta-L-malic acid)," *Journal of Controlled Release*, 122:3, 356-363 (2007).

(56) References Cited

OTHER PUBLICATIONS

Hawes, et al., "Extracellular DNA: A Bridge to Cancer" *Cancer Research*, 75(20):4260-4264 (2015).
Isenberg, et al., "Fifty years of anti-ds DNA antibodies: are we approaching journey's end?" *Rheumatology*, 46 (7):1052-1056(2007).
Jackson, et al., "Guanosine regulates adenosine levels in the kidney" *Physiol Rep*, 2(5). pii: e12028. doi: 10.14814/phy2.12028 (2014).
Kocbek, et al., "Targeting cancer cells using PLGA nanoparticles surface modified with monoclonal antibody" *Journal of Controlled Release*, 120:1-2, 18-36 (2007).
Liu, et al., "Iniparib Nonselectively Modifies Cysteine-Containing Proteins in Tumor Cells and Is Not a Bona Fide PARP Inhibitor," *Clin. Cancer Res.* 18:510-523 (2012).
Ma, et al., "Antibodies to guanosine triphosphate misidentified as anti-double-stranded DNA antibodies in a patient with antinuclear antibody-negative lupus, due to buckling of insolubilized assay DNA," *Arthritis Rheum*, 50:1533-1538 (2004).
Molfetta, et al., "Regulation of fc receptor endocytic trafficking by ubiquitination" *Front Immunol*, 5:449. Doi: 10.3389/fimmu.2014.00449 (2014).
Noble, et al. "A nucleolytic lupus autoantibody is toxic to BRCA2-deficient cancer cells" *Sci Rep*, 4:5958, 4 pages (2014).
Noble, et al., "DNA-damaging autoantibodies and cancer: the lupus butterfly theory" *Nat Rev Rheumatol*, 12(7):429-34 (2016).
Rathbone, et al., "Neurotrophic effects of extracellular guanosine" *Nucleosides Nucleotides Nucleic Acids*, 27:666-72 (2008).
Sano, et al., "DNA isolated from DNA/anti-DNA antibody immune complexes in systemic lupus erythematosus is rich in guanine-cytosine content" *J immunol*, 128:1341-1345 (1982).
Sawant, et al., "Nanosized cancer cell-targeted polymeric immunomicelles loaded with superparamagnetic iron oxide particles" *Journal of Nanoparticle Research*, 11:7, 1777-1785 (2009).
Service, et al., "Nanotechnology. Nanoparticle Trojan homes gallop from the lab into the clinic" *Science*, 330(6002):314-315 (2010).
Shin, et al., "Pharmacokinetics of guanosine in rats following intravenous or intramuscular administration of a 1:1 mixture of guanosine and acriflavine, a potential antitumor agent" *Arch Pharm Res*, 31(10):1347-53 (2008).
Shuster, et. al., "DNA hydrolyzing autoantibodies" *Science*, 1;256(5057):665-7 (1992).

Singh, et al., "A gene expression signature associated with "K-Ras addiction" reveals regulators of EMT and tumor cell survival" *Cancer Cell*, 15:489-500 (2009).
Skoulidis, et al., "Germline Brca2 heterozygosity promotes Kras(G12D)—driven carcinogenesis in a murine model of familial pancreatic cancer", *Cancer Cell*, 18:499-509 (2010).
Stollar, et al., "Nucleoside specificity in the carrier IgG-dependent induction of tolerance" *J Immunol*, 117:1308-1313 (1976).
Stroun, et al., "About the possible origin and mechanism of circulating DNA apoptosis and active DNA release" *Clin Chim Acta*, 313(1-2):139-142 (2001).
Sueoka-Aragane, et al., "Correlation between plasma DNA and tumor status in an animal model" *PloS One*, 9(12) e111881. doi: 10.1371/journal.pone.0111881 (2014).
Swystun, et al., "Breast cancer chemotherapy induces the release of cell-free DNA, a novel procoagulant stimulus" *J Thromb Haemost*, 9(11):2313-2321 (2011).
Uemura, et al., "Neurochemical analysis of focal ischemia in rats" *Stroke*, 22:1548-53 (1991).
Weisbart, et al., "Cell type specific targeted intracellular delivery into muscle of a monoclonal antibody that binds myosin IIb" *Mol Immunol*, 39(13):783-789 (2003).
Weisbart, et al., "DNA-dependent targeting of cell nuclei by a lupus autoantibody" *Sci Rep.*, 5:12022 (2015).
Wen, et al., "Extracellular DNA in pancreatic cancer promotes cell invasion and metastasis" *Cancer Research*, 73(14):4256-4266 (2013).
Wu, et al., "pH-sensitive poly(histidine)-PEG/DSPE-PEG co-polymer micelles for cytosolic drug delivery" *Biomaterials*, 34:4, 1213-1222 (2013).
Zack, et al., "Two kappa immunoglobulin light chains are secreted by an anti-DNA hybridoma: implications for isotypic exclusion" *Mol Immunol*, 32:1345-53 (1995).
Zhu, et al., "Matrix Metalloprotease 2-Responsive Multifunctional Liposomal Nanocarrier for Enhanced Tumor Targeting" *ACS Nano*, 6:4, 3491-3498 (2012).
Lin, et al., "Improved affinity of a chicken single-chain antibody to avian infectious bronchitis virus by site-directed mutagenesis of complementarity-determining region H3", *African J Biotech.*, 10(79):18294-302 (2011).
Mariuzza, et al., "The structural basis of antigen-antibody recognition", *Am Res Biophys Biophys Chem.*, 16:139-59 (1987).
McCarthy, et al., "Altering the fine specificity of an anti-legionella single chain antibody by a single amino acid insertion", *J Immunol Meth.*, 21:137-49 (2001).

\* cited by examiner

A

B

CELL PENETRATING NUCLEOLYTIC ANTIBODY BASED CANCER THERAPY

CROSS-REFERENCE TO RELATED APPLICATIONS

This application claims benefit of U.S. Provisional Application No. 62/016,960, filed Jun. 25, 2014, the contents of which are incorporated by reference herein in their entirety.

REFERENCE TO SEQUENCE LISTING

The Sequence Listing submitted Jun. 25, 2015 as a text file named "YU 6256_ST25.txt," created on Jun. 22, 2015, and having a size of 5,000 bytes is hereby incorporated by reference.

FIELD OF THE INVENTION

The invention relates to the field of anti-cancer therapy and in particular to targeted therapy for DNA repair-deficient malignancies.

BACKGROUND OF THE INVENTION

Cancer is the second most common cause of death in the U.S., exceeded only by heart disease, accounting for approximately 1 in 4 deaths. In 2014, about 585,720 Americans are expected to die of cancer, almost 1,600 people per day. As of Jan. 1, 2012, there were approximately 13.7 million Americans living with cancer, or with a history of cancer (*American Cancer Society*, Cancer Facts & Figures, 2014).

The majority of cancer therapies are severely limited by significant side effects due to non-specific tissue toxicity. The identification and development of therapeutic agents that are selectively toxic to malignant cells is a key goal in cancer research. Many tumors harbor genetic defects that distinguish them from normal cells, and some of these defects have the potential to be exploited in the development of targeted therapies for cancer. A number of tumor-specific targets are located inside cells and nuclei, and numerous types of cancer that are selectively toxic to cancer cells with pre-existing deficiencies in DNA repair are particularly vulnerable to treatments that inhibit DNA repair.

A significant amount of work has focused on applying the specific binding activity of monoclonal antibodies to the development of tumor-specific therapies. Select antibodies such as trastuzumab (HERCEPTIN®), rituximab (RITUXAN®), and cetuximab (ERBITUX®) have received approval for use in human cancer therapy. However, all of these therapeutic antibodies lack the ability to penetrate into cancer cells and are therefore limited to attacking cells with the specific antigens located on the external surface of tumor cells.

It is therefore an object of the invention to provide cell-penetrating antibodies that are selectively cytotoxic to cancer cells that are deficient in DNA repair.

It is also an object of the invention to provide compositions and methods to sensitize specific target cells to enhance and augment the efficacy of conventional therapeutic agents.

SUMMARY OF THE INVENTION

It has been established that cell-penetrating autoantibodies which are capable of damaging DNA (nucleolytic Abs) are significantly more toxic to DNA repair-deficient cells than DNA repair-proficient cells. This was demonstrated in the examples using the cell-penetrating nucleolytic mAb 5C6, which is significantly more toxic to DNA repair-deficient BRCA2$^{(-)}$ cells than their DNA repair-proficient BRCA2$^{(+)}$ counterparts. It is believed that cell-penetrating nucleolytic mAbs specifically target cancer cells that are deficient in DNA repair, such as BRCA2$^{(-)}$ cells.

Pharmaceutical compositions including one or more cell-penetrating nucleolytic antibodies or fragments thereof in an amount effective to cause DNA damage in a cell have been developed. Typically, the pharmaceutical compositions include one or more cell-penetrating nucleolytic antibodies or fragments thereof in an amount from about 0.01 mg/kg to about 100 mg/kg body weight of a human. In some embodiments the cell-penetrating nucleolytic antibody or fragment thereof is present in an amount that is effective to cause cytotoxicity to cells deficient in DNA-repair mechanisms.

An exemplary cell-penetrating nucleolytic antibody is monoclonal antibody 5C6 (mAb 5C6), or a variant or fragment thereof that binds the same epitope(s) as mAb 5C6. In preferred embodiments, the nucleolytic antibody is a humanized variant or antigen binding fragment or fusion a variant of mAb 5C6. Preferred antigen binding fragments include single chain variable fragments (scFv) of anti-guanosine antibodies, or conservative variants thereof. For example, the nucleolytic antibody can be a single chain variable fragment of mAb 5C6 (5C6 scFv), or conservative variant thereof. The 5C6 scFv can be produced as an antibody fragment including the framework regions of a human antibody. In certain embodiments, the scFv is produced as a recombinant protein expressed from an expression vector in a mammalian cell, or yeast cell such as *Pichia pastoris*. Typically, the scFv includes a heavy chain variable domain and a light chain variable domain. In some embodiments, the light chain variable domain includes the amino acid sequence of SEQ ID NO: 1, or includes one, two, or three CDRs having the amino acid sequence of SEQ ID NO: 2, SEQ ID NO: 3 or SEQ ID NO: 4, or a combination thereof. The heavy chain variable domain can include the amino acid sequence of SEQ ID NO: 5, or includes one, two, or three CDRs having the amino acid sequence of SEQ ID NO: 6, SEQ ID NO: 7 or SEQ ID NO: 8, or a combination thereof. In preferred embodiments the scFv includes six CDRs having the amino acid sequence of SEQ ID NOS: 2, 3, 4, 6, 7 and 8.

The pharmaceutical compositions can include one or more additional therapeutically active agents. Exemplary additional therapeutically active agents include antineoplastic or radio-sensitizing agents selected from the group consisting of cisplatin, cytoxan, doxorubicin, methotrexate, mitomycin c, nitrogen mustard, hydroxyurea, bevacizumab, cetuximab, rituximab, and trastuzumab tirapazamine, temozolomide, camptothecin, cisplatin, gemcitabine, 5-fluorouracil, hydroxyurea, pentoxifylline, and vinorelbine, or a combination thereof. The pharmaceutical compositions can be formulated for intravenous injection, intratumoral injection or oral administration.

Methods of treating or preventing cancer, including administering to a subject in need thereof a pharmaceutical compositions including one or more cell-penetrating nucleolytic antibodies or fragments thereof in an amount effective to cause DNA damage in a cell are provided. Typically, the methods include an amount of the one or more cell-penetrating nucleolytic antibodies or fragments thereof effective to prevent, inhibit or reduce one or more symptoms of cancer. Exemplary cancers that can be treated include breast cancers, colon cancers, endometrial tumors, brain tumors, ovarian, and pancreatic cancers, leukemias and other cancers of the blood and lymphatic system, cancers of the genitourinary system, cancers of the nervous system, cancers of the head and neck, lung cancers, gynecologic cancers, gastrointestinal cancers, skin cancers, and pediatric cancers.

The methods can be useful for treating cancer that is resistant to radiotherapy or resistant to chemotherapy.

In some embodiments the methods are useful for treating cancer that is characterized by intrinsic deficiencies in DNA repair.

In some embodiments the subject is at risk of developing cancer. The subject can be diagnosed with one or more mutations in DNA repair genes such as ATM, ATR, BRCA1, BRCA2, FANCD2, MLH1, MRE11, MSH2, PALB2, or PMS2.

The methods can also include treating the subject with radiation therapy, wherein the cell-penetrating nucleolytic antibody increases the cell's sensitivity to radiation therapy. Preferably, the methods increase the cell's sensitivity to radiation therapy by at least 10%. The cell-penetrating nucleolytic antibody can be administered to the subject at least 24 hours before the radiation therapy, concurrently with radiation therapy, or within 24 hours after radiation therapy.

The methods can also include treating the subject with chemotherapy, wherein the cell-penetrating anti-DNA antibody increases the cell's sensitivity to the chemotherapy. Preferably, the methods increase the cell's sensitivity to chemotherapy by at least 10%. The cell-penetrating nucleolytic antibody can be administered to the subject at least 24 hours before the chemotherapy, concurrently with chemotherapy, or within 24 hours after chemotherapy.

In some embodiments the cell-penetrating anti-DNA antibodies are derived from the serum of a patient with an autoimmune disease or from the serum of an animal model of an autoimmune disease. In preferred embodiments the cell-penetrating anti-DNA antibody is transported into the nucleus of the cell without the aid of a carrier or conjugate.

BRIEF DESCRIPTION OF THE DRAWINGS

FIG. 2A shows the % DNA over incubation time (minutes). FIG. 2B shows the % DNA over the concentration of antibody 5C6 (μM). FIG. 2C shows the % DNA over incubation time (hours).

FIG. 3A shows the % γH2AX expression of BRCA2$^{(-)}$ DLD1 cells in the presence of buffer only (control) or mAb 5C6 (0.25 μM), respectively. *p=0.03 (n=4). FIG. 3B shows the % growth inhibition of mAb 5C6 on the proliferation of BRCA2$^{(+)}$ and BRCA2$^{(-)}$ DLD1 cells, respectively. Error bars reflect standard error of the mean (SEM). *p=0.01 (n=6).

DETAILED DESCRIPTION OF THE INVENTION

I. Definitions

Figure 1:
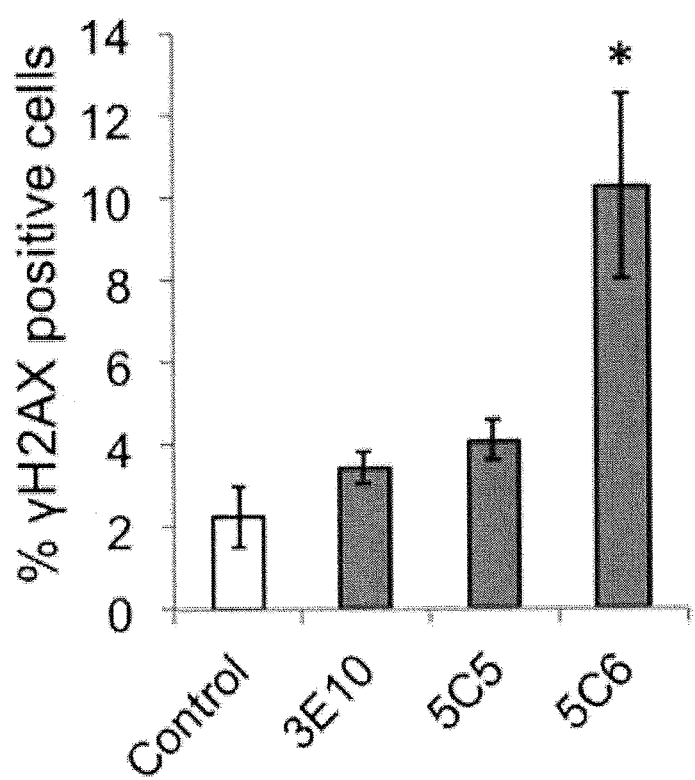
FIG. 1 is a bar graph showing the % γH2AX positive cells in the presence of buffer only (control) or mAbs 3E10, 5C5, and 5C6 (0.25 μM), respectively. Error bars reflect standard error of the mean (SEM).

The term "cell-penetrating anti-DNA antibody" refers to an immunoglobulin protein, fragment, or variant thereof that is transported into the nucleus of living mammalian cells and specifically binds to single-stranded and/or double-stranded DNA. The antibody can be transported into the nucleus of the cells without the aid of a carrier or conjugate. In some embodiments, the antibody is conjugated to a cell-penetrating moiety, such as a cell penetrating peptide.

The term "specifically binds" refers to the binding of an antibody to its cognate antigen (e.g., single-stranded and/or double-stranded DNA) while not significantly binding to other antigens.

The term "monoclonal antibody" or "mAb" refers to an antibody obtained from a substantially homogeneous population of antibodies, i.e., the individual antibodies within the population are identical except for possible naturally occurring mutations that may be present in a small subset of the antibody molecules.

The term "DNA repair" refers to a collection of processes by which a cell identifies and corrects damage to DNA molecules. Single-strand defects are repaired by base excision repair (BER), nucleotide excision repair (NER), or mismatch repair (MMR). Double-strand breaks are repaired by non-homologous end joining (NHEJ), micro-homology-mediated end joining (MMEJ), or homologous recombination. After DNA damage, cell cycle checkpoints are activated, which pause the cell cycle to give the cell time to repair the damage before continuing to divide. Checkpoint mediator proteins include BRCA1, MDC1, 53BP1, p53, ATM, ATR, CHK1, CHK2, and p21.

The term "nucleolytic" refers to an agent that can cleave the nucleotide-nucleotide linkages between nucleic acids, for example, by hydrolysis. A "nucleolytic antibody" is an antibody that can bring about and catalyze cleavage of nucleic acids, such as RNA or DNA. Nucleolytic antibodies can recognize and interact with DNA or RNA to bring about cleavage of nucleotide-nucleotide linkages at, or near to the region of contact with the DNA or RNA.

As used herein, the term "5C6" refers to a monoclonal antibody including the amino acid sequence set forth in SEQ ID NO: 1 or SEQ ID NO: 5.

As used herein, the term "scFv" as used herein means a single chain variable fragment that includes a light chain variable region (VL) and a heavy chain variable region (VH) joined by a linker. The VL and VH regions may be derived from the parent antibody or may be chemically or recombinantly synthesized.

As used herein, the term "variable region" is intended to distinguish such domain of the immunoglobulin from domains that are broadly shared by antibodies (such as an antibody Fc domain). The variable region includes a "hypervariable region" whose residues are responsible for antigen binding. The hypervariable region includes amino acid residues from a "Complementarity Determining Region" or "CDR" (i.e., typically at approximately residues 24-34 (CDR L1), 50-56 (CDR L2) and 89-97 (CDR L3) in the light chain variable domain and at approximately residues 27-35 (CDR H1), 50-65 (CDR H2) and 95-102 (CDR H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., residues 26-32 (CDR L1), 50-52 (CDR L2) and 91-96

(CDR L3) in the light chain variable domain and 26-32 (CDR H1), 53-55 (CDR H2) and 96-101 (CDR H3) in the heavy chain variable domain; Chothia and Lesk, 1987, *J. Mol. Biol.* 196:901-917).

As used herein, the term "Framework Region" or "FR" residues are those variable domain residues other than the hypervariable region residues as herein defined.

The term "polypeptide" refers to a chain of amino acids of any length, regardless of modification (e.g., phosphorylation or glycosylation). In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, a "variant," "mutant," or "mutated" polynucleotide contains at least one polynucleotide sequence alteration as compared to the polynucleotide sequence of the corresponding wild-type or parent polynucleotide. Mutations may be natural, deliberate, or accidental. Mutations include substitutions, deletions, and insertions.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and cofactors. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, and size. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Certain embodiments contemplate functional or biological equivalents of a polypeptide as set forth above. In particular, embodiments of the polypeptides can include variants having about 50%, 60%, 70%, 80%, 90%, 95%, 96%, 97%, 98%, 99%, or more sequence identity to the polypeptide of interest.

As used herein, the term "percent (%) sequence identity" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For purposes herein, the % sequence identity of a given nucleotides or amino acids sequence "C" to, with, or against a given nucleic acid sequence "D" (which can alternatively be phrased as a given sequence C that has or includes a certain % sequence identity to, with, or against a given sequence D) is calculated as follows:

$$100 \text{ times the fraction } W/Z,$$

where W is the number of nucleotides or amino acids scored as identical matches by the sequence alignment program in that program's alignment of C and D, and where Z is the total number of nucleotides or amino acids in D. It will be appreciated that where the length of sequence C is not equal to the length of sequence D, the % sequence identity of C to D will not equal the % sequence identity of D to C.

The term "impaired DNA repair" refers to a state in which a mutated cell is incapable of DNA repair or takes longer to repair damage to its DNA as compared to a wild type cell.

The term "neoplasm" or "neoplastic" refers to a cell undergoing abnormal cell proliferation.

The term "therapeutically effective" means that the amount of the composition used is of sufficient quantity to ameliorate one or more causes or symptoms of a disease or disorder. Such amelioration only requires a reduction or alteration, not necessarily elimination. A therapeutically effective amount of a composition for treating cancer is preferably an amount sufficient to cause tumor regression or to sensitize a tumor to radiation or chemotherapy.

The term "Pharmaceutically acceptable carrier" encompasses any of the standard pharmaceutical carriers, such as a phosphate buffered saline solution, water and emulsions such as an oil/water or water/oil emulsion, and various types of wetting agents. The carrier would naturally be selected to minimize any degradation of the active ingredient and to minimize any adverse side effects in the subject, as would be well known to one of skill in the art.

The term "treatment" refers to the medical management of a patient with the intent to cure, ameliorate, stabilize, or prevent one or more symptoms of a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" means to decrease one or more of an activity, symptom, response, condition, disease, or other biological parameter. This can include, but is not limited to, the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

II. Compositions

It has been established that antibodies which can penetrate the cell nuclei and inhibit DNA repair or damage DNA can effectively target cancer cells that are more sensitive to DNA damage than normal cells (i.e., DNA repair-deficient malignancies). Effective delivery of therapeutic agents to cell nuclei is challenging (Hoeijmakers, *N Engl. J. Med.* 361: 1475-1485 (2009)), but a subset of naturally occurring lupus autoantibodies which penetrate into cell nuclei are well suited to this role. Compositions for selectively targeting DNA repair-deficient malignancies are described.

A. Anti-Cancer Antibodies

Nucleolytic antibodies that selectively kill cancer cells are described. In some embodiments, the antibodies directly localize to the cell nuclei and induce DNA damage that is lethal to malignant cells that exhibit impaired DNA repair, but non-lethal to non-cancerous cells. Thus, the described antibodies selectively kill and/or sensitize malignant cells that exhibit impaired DNA repair. Autoantibodies that penetrate the cell and have nucleolytic activity are described as therapies for DNA repair-deficient malignancies.

1. Cell Penetrating Nucleolytic Antibodies

Antibodies that specifically enter into the cell to bind and damage polynucleotides are described. The antibodies bind and damage double and/or single stranded DNA, for example, by catalyzing hydrolysis of the nucleoside-nucleoside bonds. The antibodies can lack nucleic acid sequence-specificity. For example, the described antibodies can bind to and hydrolyze any double or single stranded nucleic-acid of any length. Therefore, the nucleolytic activity of a nucleolytic antibody can be specific to a particular sequence of DNA or RNA, or can occur in the absence of DNA or RNA sequence recognition and specificity.

Cell penetrating nucleolytic antibodies can be specific either for DNA or for RNA, or may hydrolyze both DNA and RNA. Typically, the cell penetrating nucleolytic antibodies degrade cytosolic RNAs and DNA. The degrading can occur within the cell nucleus. Preferably, the described antibodies specifically bind to target nucleic acids with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$, and $10^{12}$ mol$^{-1}$ or more).

Cell penetrating nucleolytic antibodies that target and damage DNA give rise to significant cytotoxicity amongst DNA repair-deficient cancer cells. In preferred embodiments, the antibodies are transported into the nucleus of the cells without the aid of a carrier or conjugate.

In other embodiments, the antibodies can be conjugated to a cell-penetrating moiety, such as a cell penetrating peptide to facilitate entry into the cell and transport to the nucleus. Examples of cell penetrating peptides include, but are not limited to, Polyarginine (e.g., $R_9$), Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol). In other embodiments, the antibody is modified using TRANSMABS™ technology (InNexus Biotech., Inc., Vancouver, BC).

In preferred embodiments, the cell-penetrating anti-DNA antibodies are lethal to cells with impaired DNA repair.

2. Sources of Cell Penetrating Nucleolytic Antibodies

Cell penetrating nucleolytic anti-cancer antibodies can be autoantibodies, such as those produced in the course of the auto-immune disease systemic lupus erythematosus (SLE). SLE is an autoimmune disease in which inappropriate production of autoantibodies results in widespread inflammation and organ dysfunction (Rahman and Isenberg, *N. Engl. J Med.* 358:929-939 (2008)). SLE is associated with an overall increased risk of malignancy but lower than expected rates of tumors associated with defects in BRCA2 such as breast, ovarian, and prostate cancers (Bernatsky, et al., *Br. J Cancer* 104:1478-1481 (2011); Bernatsky, et al., *Int. J Cancer,* 129, 2966-2969 (2011); Bernatsky, et al., *J. Autoimmun.* 42:130-135 (2013). The pathophysiology underlying this risk profile is unknown and is likely multifactorial (Bernatsky, et al., *Lupus,* 21:896-899 (2008); Bernatsky, et al., *Ann. Rheum. Dis.* 67:74-79 (2008)).

Autoantibodies to double-stranded deoxyribonucleic acid (dsDNA) are frequently identified in the serum of patients with SLE and are often implicated in disease pathogenesis. Therefore, select lupus autoantibodies are described as targeted therapies for DNA repair-deficient malignancies. In some embodiments, anti-DNA antibodies derived or isolated from patients with SLE can suppress growth of DNA repair-deficient cells, such as BRCA2$^{(-)}$ cells.

Useful cell-penetrating nucleolytic antibodies can be isolated from lymphocytes isolated from a human subject or a mouse or other experimental animal with an autoimmune disease, such as SLE. For example, nucleolytic monoclonal antibody 5C6 can be isolated from the MRL/MpJ-Fas$^{lpr}$ lupus mouse model. MRL/MpJ-Fas$^{lpr}$ mice are commercially available from multiple sources (for example, JAX® Mice, Clinical & Research Services; Stock Nos. 000485 and 006825). Isolation of antibodies can be achieved by any means known in the art, for example, by making a hybridoma from lymphocytes isolated from a human subject, or a MRL/MpJ-Fas$^{lpr}$ mouse, or other experimental animal.

Cell penetrating nucleolytic antibodies can also be produced by recombinant means, for example as a recombinant protein expressed from an expression vector in a mammalian cell, bacterial cell, or yeast cell.

The described anti-cancer antibodies can be monoclonal antibodies, or fragments or variants thereof which have bioactivity. Suitable antibodies include full-length antibodies, single chain antibodies, and antibody fragments.

In a particular embodiment, the cell penetrating nucleolytic autoantibody is the IgG2a-k monoclonal antibody 5C6 produced by MRL/MpJ-Faslpr mice. mAb 5C6 is a lupus autoantibody that was identified and tested for its effects on a matched pair of DNA repair-proficient and deficient cancer cells. mAb 5C6 selectively suppressed growth of BRCA2$^{(-)}$ DLD1 cells. Therefore, in certain embodiments, recombinant antibodies have the same or similar epitope specificity as IgG2a-k mAb 5C6 produced by MRL/MpJ-Fas$^{lpr}$ mice. This can be achieved by producing a recombinant antibody that contains the paratope of monoclonal antibody 5C6.

3. Modifications of Cell Penetrating Nucleolytic Antibodies

Cell penetrating nucleolytic antibodies can be modified to improve their therapeutic potential. For example, in some embodiments, the antibody is conjugated to another antibody specific for a second therapeutic target in the nucleus of the cancer cell. For example, the cell-penetrating nucleolytic antibody can be a fusion protein containing 5C6 Fv and a single chain variable fragment of a monoclonal antibody that specifically binds the second therapeutic target. In other embodiments, the cell-penetrating nucleolytic antibody is a bi-specific antibody having a first heavy chain and a first light chain from 5C6 and a second heavy chain and a second light chain from a monoclonal antibody that specifically binds the second therapeutic target.

i. Single Chain Variable Fragments

The single chain variable fragments described herein typically include antigen binding fragments of mAb 5C6, or a variant thereof. mAb 5C6 and active fragments and exemplary variants thereof are transported in vivo to the nucleus of mammalian cells.

The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hyper-variable regions both in the light chain and the heavy chain variable domains. The more highly conserved portions of the variable domains are called the framework (FR). The variable domains of native heavy and light chains each include four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

The fragments and fusions of antibodies described herein have bioactivity. The fragments and fusions, whether attached to other sequences or not, can include insertions, deletions, substitutions, or other selected modifications of particular regions or specific amino acids residues, provided the activity of the fragment or fusion is not significantly reduced or impaired compared to the non-modified antibody or antibody fragment.

Light Chain Variable Region

An amino acid sequence for the kappa light chain variable region (VL) of mAb 5C6 is:

```
                                        (SEQ ID NO: 1)
D I V L T Q S P A S L A A V S L G E R A T I S Y

R A S K S V S T S G Y S Y M H W N Q Q K P G Q A

P R L L I Y L V S N L E S G V P A R F S G S G S

G T D F T L N I H P V E E E D A A T Y Y C Q H I

R E L D T F F G G G T KL E I K.
```

The complementarity determining regions (CDRs) are shown with underlining, including CDR L1: R A S K S V S T S G Y S Y M H (SEQ ID NO: 2); CDR L2: L V S N L E S (SEQ ID NO: 3); CDR L3: Q H I R E L D T F (SEQ ID NO: 4).

Heavy Chain Variable Region

An amino acid sequence for the heavy chain variable region (VH) of mAb 5C6 is:

```
                                        (SEQ ID NO: 5)
Q L K L V E S G G G L V K P G G S L K L S C A A S

G F T F S S Y T M S W V R Q T P A K R L E W V A T

I S S G G G S T Y Y P D S V K G R F T I S R D N A

R N T L Y L Q M S S L R S E D T A M Y Y C A R R A

Y S K R G A M D Y W G Q G T S V T V S S.
```

The complementarity determining regions (CDRs) are shown with underlining, including CDR H1: S Y T M S (SEQ ID NO: 6); CDR H2: T I S S G G G S T Y Y P D S V K G (SEQ ID NO: 7); CDR L3: R A Y S K R G A M D Y (SEQ ID NO: 8).

ii. Linkers

The term "linker" as used herein includes, without limitation, peptide linkers. The peptide linker can be any size provided it does not interfere with the binding of the epitope by the variable regions. In some embodiments, the linker includes one or more glycine and/or serine amino acid residues.

Monovalent single-chain antibody variable fragments (scFvs) are fragments in which the carboxyl (C)-terminus of one variable domain is typically tethered to the amino (N)-terminus of the other variable domain via a 15 to 25 amino acid peptide or linker. The linker is chosen to permit the heavy chain and light chain to bind together in their proper conformational orientation.

Linkers in diabodies, triabodies, etc., typically include a shorter linker than that of a monovalent scFv as discussed above. Di-, tri-, and other multivalent scFvs typically include three or more linkers. The linkers can be the same, or different, in length and/or amino acid composition. Therefore, the number of linkers, composition of the linker(s), and length of the linker(s) can be determined based on the desired valency of the scFv as is known in the art. Preferably the linker(s) allows for or drives formation of a di-, tri-, and other multivalent scFv. For example, a linker can include 4-8 amino acids. In a particular embodiment, a linker includes the amino acid sequence GQSSRSS (SEQ ID NO: 9). In another embodiment, a linker includes 15-20 amino acids, preferably 18 amino acids. In a particular embodiment, the linker includes the amino acid sequence GQSSRSSSGGGSSGGGGS (SEQ ID NO:10). Other flexible linkers include, but are not limited to, the amino acid sequences Gly-Ser, Gly-Ser-Gly-Ser (SEQ ID NO:11), Ala-Ser, Gly-Gly-Gly-Ser (SEQ ID NO:12), (Gly$_4$-Ser)$_3$ (SEQ ID NO:13) and (Gly$_4$-Ser)$_4$ (SEQ ID NO:14), and GGSSRSSSSGGGGSGGGG (SEQ ID NO:15).

iii. Multivalent ScFvs

Divalent single-chain variable fragments (di-scFvs) can be engineered by linking two scFvs. This can be done by producing a single peptide chain with two VH and two VL regions, yielding tandem scFvs. ScFvs can also be designed with linker peptides that are too short for the two variable regions to fold together (about five amino acids), forcing scFvs to dimerize. These antibodies are known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

iv. Variants

The scFv can be composed of an antibody fragment or fusion protein including an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of mAb 5C6 (e.g., SEQ ID NO: 1 or 5), and which binds to the epitope of mAb 5C6, is selectively toxic to cancer cells or other DNA repair-deficient cells, or selectively increases the radio-sensitivity and/or chemo-sensitivity of DNA repair-deficient cells, or a combination thereof The scFv can be composed of an antibody fragment or fusion protein that includes a CDR that is at least 45%, at least 50%, at least 55%, at least 60%, at least 65%, at least 70%, at least 75%, at least 80%, at least 85%, at least 90%, at least 95%, or at least 99% identical to the amino acid sequence of a CDR of the variable heavy chain and/or light chain of mAb 5C6 (e.g., SEQ ID NO: 2, or 3, or 4; and/or 6, or 7, or 8), and which binds to the epitope of mAb 5C6, is selectively toxic to cancer cells or other DNA repair-deficient cells, or selectively increases the radio-sensitivity and/or chemo-sensitivity of DNA repair-deficient cells, or a combination thereof. The determination of percent identity of two amino acid sequences can be determined by BLAST protein comparison. In preferred embodiments, scFv includes one, two, three, four, five, or more preferably, all six of the CDRs of the above-described preferred variable domains and which binds to the epitope of mAb 5C6, is selectively lethal to cancer cells or other DNA repair-deficient cells, or selectively increases the radio-sensitivity and/or chemo-sensitivity of DNA repair-deficient cells, or a combination thereof.

In some embodiments, antibody fragment or fusion protein is modified to alter its half-life. In some embodiments, it is desirable to increase the half-life of the antibody fragment or fusion protein so that it is present in the circulation or at the site of treatment for longer periods of time. For example, where the antibody fragments or fusion proteins are being used alone to treat cancer, e.g., cancer cells having impaired DNA repair, it may be desirable to maintain titers of the antibody fragment or fusion protein in the circulation or in the location to be treated for extended periods of time. In other embodiments, the half-life of the antibody fragment or fusion protein is decreased to reduce potential side effects. For example, where the antibody fragment or fusion protein is being used in conjunction with radiotherapy or chemotherapy, the antibody fragment or fusion protein is preferably present in the circulation at high doses during the treatment with radiation or antineoplastic drug but is otherwise quickly removed from the circulation. Antibody fragments, such as mAb 5C6 scFv, are expected to have a shorter half-life than full-size antibodies. Other methods of altering half-life are known and can be used in the described methods. For example, antibody fragments and fusion proteins can be engineered with Fc variants that extend half-life, e.g., using XTEND™ antibody half-life prolongation technology (Xencor, Monrovia, Calif.).

v. Humanized Sequences

Many non-human antibodies (e.g., those derived from mice, rats, or rabbits) are naturally antigenic in humans, and thus can give rise to undesirable immune responses when administered to humans. Therefore, humanized 5C6 antibodies, antibody fragments and fusions are provided. The humanized antigen binding molecules may lessen the chance that the antibodies or antibody fragments or scFv will evoke an undesirable immune response when administered to a human.

Humanized forms of non-human (e.g., murine) antibodies include chimeric immunoglobulins, immunoglobulin chains or fragments thereof which contain minimal sequence derived from non-human immunoglobulin. Humanized antibodies include human immunoglobulins (recipient antibody) in which residues from a complementarity determining region (CDR) of the recipient antibody are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also contain residues that are found neither in the recipient antibody nor in the imported CDR or framework sequences. In general, the humanized antibody will contain substantially all of at least one, and typically two, variable domains, in which all or substantially all of the CDR regions correspond to those of a non-human immunoglobulin and all or substantially all of the FR regions are those of a human immunoglobulin consensus sequence. A humanized antibody can optimally contain at least a portion of an immunoglobulin constant region (Fc), typically that of a human immunoglobulin.

Methods for humanizing non-human antibodies are well known in the art. Generally, a humanized antibody has one or more amino acid residues introduced into it from a source that is non-human. These non-human amino acid residues are often referred to as "import" residues, which are typically taken from an "import" variable domain. Antibody humanization techniques generally involve the use of recombinant DNA technology to manipulate the DNA sequence encoding one or more polypeptide chains of an antibody molecule. Humanization can be essentially performed by substituting rodent CDRs or CDR sequences for the corresponding sequences of a human antibody. Accordingly, a humanized form of a non-human antibody (or a fragment thereof) is a chimeric antibody or fragment, wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important in order to reduce antigenicity. According to the "best-fit" method, the sequence of the variable domain of a rodent antibody is screened against the entire library of known human variable domain sequences. The human sequence which is closest to that of the rodent is then accepted as the human framework (FR) for the humanized antibody. Another method uses a particular framework derived from the consensus sequence of all human antibodies of a particular subgroup of light or heavy chains. The same framework may be used for several different humanized antibodies.

It is important that antibodies be humanized with retention of high affinity for the antigen and other favorable biological properties. To achieve this goal, humanized antibodies are preferably prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding.

4. Additional Domains and Moieties

In some embodiments the therapeutic function of the antibody is enhanced by coupling the antibody or a fragment thereof with an additional therapeutic agent. Such coupling of the antibody or fragment with the additional therapeutic agent can be achieved by making an immune-conjugate or by making a fusion protein, or by linking the antibody or fragment to a nucleic acid such as siRNA, comprising the antibody or antibody fragment and the therapeutic agent.

A recombinant fusion protein is a protein created through genetic engineering of a fusion gene. This typically involves removing the stop codon from a cDNA sequence coding for the first protein, then appending the cDNA sequence of the second protein in frame through ligation or overlap extension PCR. The DNA sequence will then be expressed by a cell as a single protein. The protein can be engineered to include the full sequence of both original proteins, or only a portion of either. If the two entities are proteins, often linker (or "spacer") peptides are also added which make it more likely that the proteins fold independently and behave as expected.

In some embodiments, the cell-penetrating antibody is modified to alter its half-life. In some embodiments, it is desirable to increase the half-life of the antibody so that it is present in the circulation or at the site of treatment for longer periods of time. For example, where the anti-DNA antibodies are being used alone to treat cancer, e.g., cancer cells having impaired DNA repair, it may be desirable to maintain titers of the antibody in the circulation or in the location to be treated for extended periods of time. In other embodiments, the half-life of the anti-DNA antibody is decreased to reduce potential side effects. For example, where the antibody is being used in conjunction with radiotherapy or chemotherapy, the antibody is preferably present in the circulation at high doses during the treatment with radiation or antineoplastic drug but is otherwise quickly removed from the circulation. Antibody fragments, such as 5C6 Fv are expected to have a shorter half-life than full size antibodies. Other methods of altering half-life are known and can be used in the described methods. For example, antibodies can be engineered with Fc variants that extend half-life, e.g., using XTEND™ antibody half-life prolongation technology (Xencor, Monrovia, Calif.).

B. Pharmaceutical Compositions

The cell penetrating nucleolytic antibodies can be used therapeutically in combination with a pharmaceutically acceptable carrier. The materials may be in solution, emulsions, or suspension (for example, incorporated or formed into nanoparticles, microparticles, liposomes, or cells). Typically, an appropriate amount of a pharmaceutically-acceptable salt is used in the formulation to render the formulation isotonic. Examples of pharmaceutically-acceptable carriers include, but are not limited to, saline, Ringer's solution and dextrose solution. The pH of the solution is preferably from about 5 to about 8, and more preferably from about 7 to about 7.5. Pharmaceutical compositions may include carriers, thickeners, diluents, buffers, preservatives, and surface active agents. Further carriers include sustained release preparations such as semi-permeable matrices of solid hydrophobic polymers containing the antibody, which matrices are in the form of shaped particles, e.g., films, liposomes or microparticles. It will be apparent to those persons skilled in the art that certain carriers may be more preferable depending upon, for instance, the route of administration and concentration of composition being administered. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Parenteral vehicles include sodium chloride solution, Ringer's dextrose, dextrose and sodium chloride, lactated Ringer's, or fixed oils. Preservatives and other additives may also be present such as, for example, antimicrobials, antioxidants, chelating agents, and inert gases.

To aid dissolution of antibodies into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose and carboxymethyl cellulose. These surfactants could be present in the formulation of the protein or derivative either alone or as a mixture in different ratios. Additives which potentially enhance uptake of peptides are for instance the fatty acids oleic acid, linoleic acid and linolenic acid.

The cell penetrating nucleolytic antibodies can be administered and taken up into the cells of a subject with or without the aid of a delivery vehicle. Appropriate delivery vehicles for the described nucleolytic antibodies are known in the art and can be selected to suit the particular nucleolytic antibody or therapeutic target.

Micro and nanoparticles designed to deliver cargo such as drugs and antibodies to the vasculature, to organs or tissues are known in the art.

For example, perfluorocarbon nanoparticles, previously considered as artificial blood substitutes, have been developed into a platform technology for molecular imaging and targeted drug delivery, i.e., a so-called "theranostic" technology. These lipid-encapsulated particles, which are nominally 250 nm in diameter, can be administered intravenously and are typically constrained by size to the intact vasculature.

In some embodiments the delivery vehicle is a liposome. Liposomes are disclosed for the delivery of the described cell penetrating nucleolytic antibodies directly to a certain target cell type, for example cancer cells. Target cells can internalize liposomes, leading to the delivery of the one or more cell penetrating nucleolytic antibodies to the intracellular compartments of the target cell.

Suitable methods, materials and lipids for making liposomes are known in the art. Liposome delivery vehicles are commercially available from multiple sources. Liposomes can be formed from a single lipid bilayer (i.e., the liposome can be unilamellar) or several concentric lipid bilayers (i.e., the liposome can be multilamellar). The liposome may be formed from a single lipid; however, in some embodiments, the liposome is formed from a combination of more than one lipid. The lipids can be neutral, anionic or cationic at physiologic pH.

C. Targeting Moieties

In some embodiments, compositions of cell penetrating nucleolytic antibodies include a targeting signal, a protein transduction domain or a combination thereof. The targeting moiety can be attached or linked directly or indirectly to the cell penetrating nucleolytic antibodies. For example, in some embodiments, delivery vehicles used to deliver the cell penetrating nucleolytic antibodies include targeting molecules. These can be coupled to the delivery vehicles using standard techniques. In some embodiments, the targeting moiety is attached or linked to a delivery vehicle such as a nanoparticle or a microparticle.

Targeting molecules can be proteins, peptides, nucleic acid molecules, saccharides or polysaccharides that bind to a receptor or other molecule on the surface of a targeted cell. The degree of specificity can be modulated through the selection of the targeting molecule. For example, antibodies are very specific. These can be polyclonal, monoclonal, fragments, recombinant, or single chain, many of which are commercially available or readily obtained using standard techniques.

The targeting signal or sequence can be specific for a host, tissue, organ, cell, organelle, non-nuclear organelle, or cellular compartment. Moreover, the compositions described here can be targeted to other specific intercellular regions, compartments, or cell types.

In one embodiment, the targeting signal binds to its ligand or receptor which is located on the surface of a target cell such as to bring the cell penetrating nucleolytic antibodies and cell membranes sufficiently close to each other to allow penetration of the antibody into the cell. Additional embodiments are directed to specifically delivering cell penetrating nucleolytic antibodies to specific tissue or cell types with cancer activity. In a preferred embodiment, the targeting molecule is an antibody or antigen binding fragment thereof, an antibody domain, an antigen, a T-cell receptor, a cell surface receptor, a cell surface adhesion molecule, a major histocompatibility locus protein, a viral envelope protein and a peptide selected by phage display that binds specifically to a defined cell.

Ligands can be attached to polymeric particles indirectly though adaptor elements which interact with the polymeric particle. Adaptor elements may be attached to polymeric particles in at least two ways. The first is during the preparation of the micro- and nanoparticles, for example, by incorporation of stabilizers with functional chemical groups during emulsion preparation of microparticles. For example, adaptor elements, such as fatty acids, hydrophobic or amphiphilic peptides and polypeptides can be inserted into the particles during emulsion preparation. In a second embodiment, adaptor elements may be amphiphilic molecules such as fatty acids or lipids which may be passively adsorbed and adhered to the particle surface, thereby introducing functional end groups for tethering to ligands. Adaptor elements may associate with micro- and nanoparticles through a variety of interactions including, but not limited to, hydrophobic interactions, electrostatic interactions and covalent coupling.

Exemplary targeting signals include an antibody or antigen binding fragment thereof specific for a receptor expressed at the surface of a target cell or other specific antigens, such as cancer antigens.

Representative receptors include but are not limited to growth factors receptors, such as epidermal growth factor receptor (EGFR; HER1; c-erbB2 (HER2); c-erbB3 (HER3); c-erbB4 (HER4); insulin receptor; insulin-like growth factor receptor 1 (IGF-1R); insulin-like growth factor receptor 2/Mannose-6-phosphate receptor (IGF-II R/M-6-P receptor); insulin receptor related kinase (IRRK); platelet-derived growth factor receptor (PDGFR); colony-stimulating factor-1receptor (CSF-1R) (c-Fms); steel receptor (c-Kit); Flk2/Flt3; fibroblast growth factor receptor 1 (Flg/Cek1); fibroblast growth factor receptor 2 (Bek/Cek3/K-Sam); Fibroblast growth factor receptor 3; Fibroblast growth factor receptor 4; nerve growth factor receptor (NGFR) (TrkA); BDNF receptor (TrkB); NT-3-receptor (TrkC); vascular endothelial growth factor receptor 1 (Flt1); vascular endothelial growth factor receptor 2/Flk1/KDR; hepatocyte growth factor receptor (HGF-R/Met); Eph; Eck; Eek; Cek4/Mek4/HEK; Cek5; Elk/Cek6; Cek7; Sek/Cek8; Cek9; Cek10; HEK11; 9 Ror1; Ror2; Ret; Ax1; RYK; DDR; and Tie.

In some embodiments, the targeting signal is or includes a protein transduction domain (PTD), also known as cell penetrating peptides (CPPS). PTDs are known in the art, and include but are not limited to small regions of proteins that are able to cross a cell membrane in a receptor-independent mechanism (Kabouridis, P., *Trends in Biotechnology* (11): 498-503 (2003)). The two most commonly employed PTDs are derived from TAT (Frankel and Pabo, Cell, 55(6):1189-93 (1988)) protein of HIV and Antennapedia transcription factor from *Drosophila*, whose PTD is known as Penetratin (Derossi et al., *J. Biol. Chem.* 269(14):10444-50 (1994)).

Examples of molecules targeting extracellular matrix ("ECM") include glycosaminoglycan ("GAG") and collagen. In one embodiment, the external surface of a delivery vehicle or microparticle may be modified to enhance the ability of the microparticles to interact with selected cells or tissue. In another embodiment, the outer surface of a polymer microparticle having a carboxyl terminus may be linked to PAMPs that have a free amine terminus. The PAMP targets Toll-like Receptors (TLRs) on the surface of the cells or tissue, or signals the cells or tissue internally, thereby potentially increasing uptake. PAMPs conjugated to the particle surface or co-encapsulated may include: unmethylated CpG DNA (bacterial), double-stranded RNA (viral), lipopolysacharride (bacterial), peptidoglycan (bacterial), lipoarabinomannin (bacterial), zymosan (yeast), mycoplasmal lipoproteins such as MALP-2 (bacterial), flagellin (bacterial) poly(inosinic-cytidylic) acid (bacterial), lipoteichoic acid (bacterial) or imidazoquinolines (synthetic).

IV. Methods of Use

Methods of using the described cell penetrating nucleolytic antibodies are provided. The methods can include administering to a subject an effective amount of a composition including one or more cell penetrating nucleolytic antibodies to prevent, reduce, or inhibit the growth of DNA repair-deficient cells in the subject.

A. Methods of Treatment

Cell penetrating nucleolytic antibodies can be used to specifically target and eliminate DNA-repair deficient malignant cells through either local or systemic delivery. In some embodiments, the compositions are administered systemically. Delivery vehicles can be selected and used to target the cell penetrating nucleolytic antibodies to a particular location or cell type. In other embodiments, the cell penetrating nucleolytic antibodies are directly administered to a target tissue. In further embodiments, the route of administration targets the cell penetrating nucleolytic antibodies directly to a specific organ or to tissue.

The compositions described herein can reduce or prevent the growth of DNA repair-deficient cancer cells, but allow the growth of DNA repair-competent tissue to occur. Exemplary DNA repair-deficient cancer cells include BRCA2$^{(-)}$ cells. In some embodiments methods of treatment with the described compositions selectively suppresses the growth of cancer cells. In some embodiments, the methods include suppressing the growth of cancer cells through a mechanism that is independent of necrosis or apoptosis. The methods can include suppressing the growth of cancer cells by inducing senescence specifically in cancer cells.

Methods of treatment and prevention of diseases and disorders using the described cell penetrating nucleolytic antibodies optionally including a delivery vehicle are discussed in more detail below.

All of the described methods can also include the step of identifying a subject in need of treatment. In certain embodiments the subject in need of treatment has been identified as having one or more diseases, such as malignancies, or has been identified as having a predisposition to acquired one or more diseases, such as malignancies.

1. Controls

The effect of a cell penetrating nucleolytic antibody can be compared to a control. Suitable controls are known in the art and include, for example, untreated cells or an untreated subject. In some embodiments, the control is untreated tissue from the same subject that is treated, or from a different, untreated subject. Preferably the cells or tissue of the control are derived from the same tissue as the treated cells or tissue. In some embodiments, an untreated control subject suffers from the same disease or condition as the treated subject. For example, in some embodiments, one or more of the pharmacological or physiological markers or pathways affected by cell penetrating nucleolytic antibodies is compared to the same pharmacological or physiological marker or pathway in untreated control cells or untreated control subjects. In some embodiments, cell penetrating nucleolytic antibody-treated subjects are compared to subjects treated with other antineoplastic drugs, such as alkylating agents, antimetabolites, anthracyclines, plant alkaloids, topoisomerase inhibitors, monoclonal antibodies, or other anti-tumor agents. The subjects treated with other antineoplastic drugs can have a greater incidence of toxic side effects or proliferation of cancer cells than do subjects treated with the cell penetrating nucleolytic antibodies.

2. Dosage Regimens, Route of Administration

Pharmaceutical compositions including one or more cell penetrating nucleolytic antibodies can be administered in a variety of manners, depending on whether local or systemic treatment is desired, and depending on the area to be treated. For example, the described compositions can be administered intravenously, intraperitoneally, intramuscularly, subcutaneously, intracavity, or transdermally. The compositions may be administered parenterally (e.g., intravenously), by intramuscular injection, by intraperitoneal injection, transdermally, extracorporeally, topically or the like, including topical intranasal administration or administration by inhalation.

Parenteral administration of the composition, if used, is generally characterized by injection. Injectable formulations can be prepared in conventional forms, either as liquid solutions or suspensions, solid forms suitable for solution of suspension in liquid prior to injection, or as emulsions. Administration involving use of a slow release or sustained release system, such that a constant dosage is maintained, is also discussed.

In certain embodiments, the compositions are administered locally, for example by injection directly into a site to be treated, such as the tumor. In certain embodiments cell penetrating nucleolytic antibodies can be administered directly to a tumor. In further embodiments, the compositions are injected or otherwise administered directly to one or more surgical sites where tumors have been removed. In some embodiments cell penetrating nucleolytic antibodies delivered locally result in concentrations that are twice, 10 times, 100 times, 500 times, 1000 times or more than 1000 times greater than that achieved by systemic administration of the same compound. In some embodiments the locally administered cell penetrating nucleolytic antibodies are steadily released at the site of delivery at a constant rate over a period of time. Preferably, the steady release maintains a desired concentration of the cell penetrating nucleolytic antibodies at the site of delivery.

The subject can be administered one or more doses of the composition every 1, 2, 3, 4, 5, 6, 7, 14, 21, 28, 35, or 48 days after initiation of treatment. In some embodiments, the multiple doses of the compositions are administered before an improvement in disease condition is evident. For example, in some embodiments, the subject receives 1, 2, 3, 4, 5, 6 7, 14, 21, 28, 35, or 48, over a period of 1, 2, 3, 4, 5, 6 7, 14, 21, 28, 35, or 48 days or weeks before an improvement in the disease or condition is evident.

Thus, the described compositions including one or more cell penetrating nucleolytic antibodies can be administered at different times in relation to a diagnosis, prognosis or surgery, depending on the cancer to be treated. The timing of commencement of cell penetrating nucleolytic antibody therapy should be determined based upon the needs of the subject, and can vary from at the time of diagnosis or procedure, such as radiotherapy, surgery or other chemotherapy, to one or more days, weeks or months after a diagnosis or procedure. Methods for using formulations for delayed release of cell penetrating nucleolytic antibodies are provided. In some embodiments, therapy using cell penetrating nucleolytic antibodies can be discontinued once cancer-tissue cytotoxicity has occurred.

3. Effective Amounts

In some in vivo approaches, the compositions of cell penetrating nucleolytic antibody or fragment thereof are administered to a subject in a therapeutically effective amount. In some embodiments, the pharmaceutical composition is a unit dosage containing one or more cell penetrating nucleolytic antibodies in a pharmaceutically acceptable excipient, wherein one or more antibodies is present in an amount effective to inhibit DNA repair in a cancer cell. In certain embodiments, the cell penetrating nucleolytic antibody is present in amount from about 200 mg/m$^2$ to about 1000 mg/m$^2$, including about 200, 250, 300, 350, 400, 450, 500, 600, 700, 800, 900, or 1000 mg/m$^2$. In some embodiments, the unit dosage is in a unit dosage form for intravenous injection. In some embodiments, the unit dosage is in a unit dosage form for oral administration. In some embodiments, the unit dosage is in a unit dosage four for intratumoral injection.

For all of the described compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatment desired. Generally dosage levels of between 0.001 and 100 mg/kg of body weight daily are administered to mammals, most preferably, humans. Generally, for intravenous injection or infusion, dosage may be lower. Preferably, the compositions are formulated to achieve a cell penetrating nucleolytic antibody serum level of between about 1 and about 1000 μM.

In some embodiments, the cell penetrating nucleolytic antibodies are effective to prevent the growth of DNA-repair deficient cancer cells, such as BRCA2$^{(-)}$ cells. For example, one or more cell penetrating nucleolytic antibodies can be in an amount effective to kill DNA-repair deficient cancer cells, but have no cytotoxic effect upon non-cancer cells.

In some embodiments the cell penetrating nucleolytic antibodies induce replicative or cellular senescence in cancer cells. Senescence is a process leading to irreversible arrest of cell division which was first described in cultures of human fibroblasts that lost the ability to divide upon continuous subculture (Hayflick, *Exp. Cell Res.*, 37:614-636 (1965)). Since then, replicative senescence has been shown in various mammalian tissues in culture and in vivo (Dimri, et al., *Proc. Natl. Acad. Sci. USA*, 92:9363-9367 (1995); Stanulis-Praeger, et al., *Mech. Ageing Dev.*, 38:1-48 (1987)). Contrary to normal somatic cells, most tumors have extended or infinite life spans. Cellular and viral oncogenes, or the loss of tumor suppressors, are involved in the transformation and immortalization of primary cells. Inactivation of the p53 and p16INK4a tumor suppressors is among the most common events in human cancers. Therefore, in some embodiments one or more cell penetrating nucleolytic antibodies are in an amount effective to induce senescence in cancer cells in a subject compared to an untreated control.

In one embodiment one or more cell penetrating nucleolytic antibody are in an amount effective to prevent or reduce the symptoms of cancer in a subject compared to an untreated control. Preferably the amount of one or more cell penetrating nucleolytic antibody does not prevent the growth of non-cancer cells.

4. Cancers to be Treated

In preferred embodiments, one or more cell penetrating nucleolytic antibodies are effective to prevent, reduce, inhibit, or delay one or more symptoms of a cancer in a subject. Thus, the described cell penetrating nucleolytic antibodies have a wide variety of therapeutic and prophylactic uses.

Cells undergoing unregulated growth, invasion, or metastasis are generally referred to as cancerous, neoplastic or transformed cells. Typically, the growth of a cancerous or neoplastic cell exceeds and is not coordinated with that of the normal, non-cancerous tissues around it. The growth can persist in the same excessive manner even after cessation of a pro-proliferative stimuli, and typically causes formation of a tumor. Neoplasms may be benign, pre-malignant or malignant.

i. DNA Repair-Deficient Malignancies

Cancerous cells can exhibit impaired DNA repair. In preferred embodiments, the cells are defective in the expression of a gene involved in DNA repair, DNA synthesis, or homologous recombination. Exemplary genes include XRCC1, ADPRT (PARP-1), ADPRTL2, (PARP02) CTPS, MLH1, MSH2, FANCD2, PMS2, p53, p21, PTEN, RPA, RPA1, RPA2, RPA3, XPD, ERCC1, XPF, MMS19, RAD51, RAD51.beta., RAD51C, RAD51D, DMC1, XRCCR, XRCC3, BRCA1, BRCA2, RAD52, RAD54, RAD50, MRE11, NB51, WRN, BLM KU70, KU80, ATM ATR CHK1, CHK2, FANCA, FANCB, FANCC, FANCD1, FANCD2, FANCE, FANCF, FANCG, FANCC, FANCD1, FANCD2, FANCE, FANCF, FANCG, RAD1, and RAD9. In some embodiments, the defective gene is a tumor-suppressor gene.

ii. BRCA

Cancer cells deficient in DNA repair can have one or more mutations in the BRCA1 or BRCA2 genes. The official name (breast cancer 2, early onset) BRCA2 is a human tumor suppressor gene (specifically, a caretaker gene), found in all humans. The BRCA2 protein, also known as breast cancer type 2 susceptibility protein, is responsible for repairing DNA. BRCA2 and BRCA1 are normally expressed in the cells of breast and other tissues, where they help repair damaged DNA or destroy cells if DNA cannot be repaired. They are involved in the repair of chromosomal damage with an important role in the error-free repair of DNA double strand breaks. If BRCA1 or BRCA2 itself is damaged by a BRCA mutation, damaged DNA is not repaired properly, and this increases the risk for breast cancer. BRCA2 plays an important role in homology-directed repair of DNA double-strand breaks and BRCA2-deficient (BRC2A$^{(-)}$) cells therefore have an intrinsic deficiency in DNA repair. Gene mutations, such as BRCA1 and BRCA2 mutations, can be identified using standard PCR, hybridization, or sequencing techniques. Cancers that are commonly associated with mutations in the BRCA1 or BRCA2 genes include, but are not limited to colon, breast and prostate cancers.

Methods of using one or more cell penetrating nucleolytic antibodies for treating a cancer characterized by the proliferation of DNA repair-deficient cells are described. The antibodies can be used to treat cells undergoing unregulated growth, invasion, or metastasis including but not limited to breast cancer, ovarian cancer and prostate cancer.

Therefore, in some embodiments, the cell penetrating nucleolytic antibodies can be used to treat cancers arising from DNA repair deficient familial syndromes, such as breast, ovarian, and pancreatic cancers. In these embodiments, the cell penetrating nucleolytic antibodies can be effective without radiotherapy or chemotherapy. For example, the cell penetrating nucleolytic antibodies can be used to treat cancers that are linked to mutations in BRCA1, BRCA2, PALB2, or related genes. The cell penetrating nucleolytic antibodies can also be used to treat colon cancers, endometrial tumors, or brain tumors linked to mutations in genes associated with DNA mismatch repair, such as MSH2, MLH1, PMS2, and related genes. The cell penetrating nucleolytic antibodies can also be used to treat cancers with silenced DNA repair genes, such as BRCA1, MLH1. In these preferred embodiments, the ability of the cell penetrating nucleolytic antibodies to inhibit DNA repair combined with the inherent repair deficiencies of these cancers can be sufficient to induce cell death.

iii. Other Malignancies

The cell penetrating nucleolytic antibodies can be used in combination with radiotherapy, chemotherapy, or a combination thereof, to treat any cancer, including carcinomas, gliomas, sarcomas, or lymphomas. In these embodiments, the anti-DNA antibodies can sensitize the cells to the DNA-damaging effects of radiotherapy or chemotherapy. A representative but non-limiting list of cancers that the described compositions of nucleolytic antibodies, fragments, fusions and variants thereof can be used to treat include cancers of the blood and lymphatic system (including leukemias, Hodgkin's lymphomas, non-Hodgkin's lymphomas, solitary plasmacytoma, multiple myeloma), cancers of the genitourinary system (including prostate cancer, bladder cancer, renal cancer, urethral cancer, penile cancer, testicular cancer,), cancers of the nervous system (including mengiomas, gliomas, glioblastomas, ependymomas) cancers of the head and neck (including squamous cell carcinomas of the oral cavity, nasal cavity, nasopharyngeal cavity, oropharyngeal cavity, larynx, and paranasal sinuses), lung cancers (including small cell and non-small cell lung cancer), gynecologic cancers (including cervical cancer, endometrial cancer, vaginal cancer, vulvar cancer ovarian and fallopian tube cancer), gastrointestinal cancers (including gastric, small bowel, colorectal, liver, hepatobiliary, and pancreatic cancers), skin cancers (including melanoma, squamous cell carcinomas, and basal cell carcinomas), breast cancer (including ductal and lobular cancer), and pediatric cancers (including neuroblastoma, Ewing's sarcoma, Wilms tumor, medulloblastoma).

In some embodiments, the cancer is a neoplasm or tumor that demonstrates some resistance to radiotherapy or chemotherapy. Cancers that are resistant to radiotherapy using standard methods include sarcomas, lymphomas, leukemias, carcinomas, blastomas, and germ cell tumors.

B. Combination Therapies

The described compositions including cell penetrating nucleolytic antibodies can be administered alone, or in combination with one or more additional active agent(s), or treatment processes as part of a therapeutic or prophylactic treatment regime.

1. Additional Therapeutic Agents

In some embodiments compositions including one or more cell penetrating nucleolytic antibodies are administered in combination with one or more additional therapeutic agents. The term "combination" or "combined" is used to refer to either concomitant, simultaneous, or sequential administration of two or more agents. Therefore, the combinations can be administered either concomitantly (e.g., as an admixture), separately but simultaneously (e.g., via separate intravenous lines into the same subject), or sequentially (e.g., one of the compounds or agents is given first followed by the second).

For example, the composition can be administered on the first, second, third, or fourth day, or combinations thereof. The composition can be administered on the same day, or a different day than the one or more additional active agents.

The additional therapeutic agents can be chemotherapeutic drugs including, but not limited to, alkylating agents, antimetabolites, anthracyclines, plant alkaloids, topoisomerase inhibitors, monoclonal antibodies, and other anti-tumor agents.

In some embodiments, the additional therapeutic agents are antineoplastic drugs that damage DNA or interfere with DNA repair. These antineoplastic drugs can synergize effectively with the cell penetrating nucleolytic antibodies. In these embodiments, the antibody increases the cell's sensitivity to the chemotherapy by at least 5%, 10%, 15%, 20%, 25%, 30%, 35%, 40%, 45%, 50% or more than 50%.

Non-limiting examples of antineoplastic drugs that damage DNA or inhibit DNA repair include carboplatin, carmustine, chlorambucil, cisplatin, cyclophosphamide, dacarbazine, daunorubicin, doxorubicin, epirubicin, idarubicin, ifosfamide, lomustine, mechlorethamine, mitoxantrone, oxaliplatin, procarbazine, temozolomide, and valrubicin. In some embodiments, the antineoplastic drug is temozolomide, which is a DNA damaging alkylating agent commonly used against glioblastomas.

In a particular embodiment, one antineoplastic drug is a PARP inhibitor, which inhibits a step in base excision repair of DNA damage. In some embodiments, the additional antineoplastic drug is a histone deacetylase inhibitor, which suppresses DNA repair at the transcriptional level and disrupt chromatin structure.

In other embodiments, one or more additional antineoplastic drugs complement the anti-DNA antibodies by targeting a different activity in the cancer cell. In these embodiments, the antineoplastic drug does not inhibit DNA repair or damage DNA.

Examples of antineoplastic drugs that can be combined with the cell-penetrating anti-DNA antibodies include, but are not limited to, alkylating agents (such as temozolomide, cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil, gemcitabine, methotrexate, cytosine arabinoside, fludarabine, and floxuridine), anti-mitotics (including taxanes such as paclitaxel and decetaxel, and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), and topoisomerase inhibitors (including camptothecins such as irinotecan and topotecan and derivatives of epipodophyllotoxins such as amsacrine, etoposide, etoposide phosphate, and teniposide).

In further embodiments, the additional active agents can be other antibodies. The other antibodies can be cell penetrating antibodies, such as the anti-DNA antibody 3E10, 4H2 or 5C5. Monoclonal antibody 3E10 and 3E10 Fv, without being conjugated to any therapeutic protein, enhances cancer cell radio-sensitivity and chemo-sensitivity and this effect is potentiated in cells deficient in DNA repair, as described in U.S. Pat. Nos. 4,812,397 and 7,189,396, U.S. Published Application No. 2014/0050723, and PCT/US2012/31860.

In yet further embodiments, the additional active agents can be antibiotics, antivirals, steroidal and non-steroidal anti-inflammatories, conventional immunotherapeutic agents, immune-suppressants, cytokines, chemokines and/or growth factors, anti-proliferatives or anti-migration agents.

2. Radiotherapy

In some embodiments compositions including one or more cell penetrating nucleolytic antibodies are administered in combination with radiotherapy. Radiation therapy (radiotherapy) is the medical use of ionizing radiation as part of cancer treatment to control malignant cells. Radiotherapy also has several applications in non-malignant conditions, such as the treatment of trigeminal neuralgia, severe thyroid eye disease, pterygium, pigmented villonodular synovitis, prevention of keloid scar growth, and prevention of heterotopic ossification. In some embodiments, anti-DNA antibodies are used to increase sensitivity to radiotherapy (radio-sensitivity) for a non-malignant condition.

Radiation therapy works by damaging the DNA of dividing cells, e.g., cancer cells. This damage is either direct or indirect. Indirect ionization happens as a result of the ionization of water, forming free radicals, notably hydroxyl radicals, which then damage the DNA. Direct damage to cancer cell DNA occurs through high-LET (linear energy transfer) usually causing double-stranded DNA breaks.

The amount of radiation used in photon radiation therapy is measured in Gray (Gy), and varies depending on the type and stage of cancer being treated. For curative cases, the typical dose for a solid epithelial tumor ranges from 60 to 80 Gy, while lymphomas are treated with 20 to 40 Gy. Postoperative (adjuvant) doses are typically around 45-60 Gy in 1.8-2 Gy fractions (for breast, head, and neck cancers).

The response of a cancer to radiation is described by its radio-sensitivity. Highly radio-sensitive cancer cells are rapidly killed by modest doses of radiation. These include leukemias, most lymphomas and germ cell tumors. The majority of epithelial cancers are only moderately radiosensitive, and require a significantly higher dose of radiation (60-70 Gy) to achieve a radical cure. Some types of cancer are notably radio-resistant, that is, much higher doses are required to produce a radical cure than may be safe in clinical practice. Renal cell cancer and melanoma are generally considered to be radio-resistant.

In some embodiments, the described cell-penetrating nucleolytic antibodies serve the function of enhancing the radio-sensitivity of cancers. In these embodiments, the cell-penetrating nucleolytic antibodies increase the cell's sensitivity to the radiotherapy by at least 10%, 15%, 20%, 25%, 30%, 35%, 40%, 45%, or 50%. Moreover, the described cell penetrating anti-DNA antibodies can be combined with one or more additional radio-sensitizers. Examples of known radio-sensitizers include cisplatin, gemcitabine, 5-fluorouracil, pentoxifylline, and vinorelbine.

EXAMPLES

Example 1

5C6 is a Lupus Autoantibody that Penetrates into Cell Nuclei

Materials and Methods

Hybridomas and Cell Lines

A panel of hybridomas, including the 3E10, 5C5, and 5C6 hybridomas was previously generated from the MRLmpj/lpr lupus mouse model and DNA binding activity was evaluated (Zack, et al., *J. Immunol.* 154:1987-1994 (1995); Gu, et al., *J. Immunol.*, 161:6999-7006 (1998)). The hybridomas were maintained in serum free hybridoma media (BD Cell MAb medium; BD Biosciences, San Jose, Calif.) supplemented with 2 mM L-glutamine (Life Technologies, Carlsbad, Calif.). Antibodies were harvested in hybridoma supernatants and exchange-dialyzed into appropriate media. BRCA2 proficient (BRCA2$^{(+)}$ and deficient (BRCA2$^{(-)}$) DLD1 colon cancer cells (Horizon Discovery, Ltd., Cambridge, UK) were grown in RPMI 1640 (Life Technologies) supplemented with 10% fetal bovine serum (FBS; Sigma-Aldrich, Saint Louis, Mo.). The identities of the BRCA2$^{(+)}$ and BRCA2$^{(-)}$ DLD1 colon cancer cells were confirmed by verifying differential sensitivity to ionizing radiation (not shown).

Cell-Penetration Assays

DLD1 cells grown on glass coverslips were treated with control buffer or 6.6 µM 3E10, 5C5, or 5C6 for three hours. Cells were then washed with PBS, fixed with chilled 100% ethanol for 5 minutes, washed again with PBS, and then probed with Alexa 488-conjugated goat anti-mouse IgG antibody overnight at 4° C. (Cell Signaling, Danvers, Mass.). To counterstain the nucleus, PI at 1 µg/ml was added to the cells for 30 minutes. Nuclear penetration by the antibodies was then imaged using an EVOS fl digital fluorescence microscope (Advanced Microscopy Group, Bothell, Wash.) using green fluorescent protein (GFP) filter (40× magnification; Life Technologies). Light and fluorescent images under GFP and RFP filters were observed and merged images were used to confirm nuclear localization by 5C6.

Results

A panel of lupus autoantibodies from the MRL-mpj/lpr mouse model of SLE was established (Zack, et al., *J. Immunol.* 154:1987-1994 (1995)), and this panel includes cell-penetrating and nuclear-localizing anti-DNA antibodies 3E10, 5C5, and 5C6 (Gu, et al., *J. Immunol.* 161:6999-70067 (1998)). 3E10 does not appear to damage DNA but has been shown to inhibit DNA repair (Hansen, et al., *Science Translational Medicine,* 4:157ra1426 (2012)). The effects of 5C5 and 5C6 on DNA integrity have not previously been tested, and it has not previously been determined whether these antibodies damage DNA in cells. The matched pair of BRCA2$^{(+)}$ and BRCA2$^{(-)}$ DLD1 human colon cancer cells was selected for these experiments because they are genetically identical with the exception of the functional status of BRCA2 (Liu, et al., Clin. Cancer Res. 18:510-523 (2012)). BRCA2 is key player in homology-directed repair of DNA double-strand breaks, and cells deficient in BRCA2 are therefore highly sensitive to DNA damaging agents.

As a first step the ability of 3E10, 5C5, and 5C6 to penetrate into DLD1 cell nuclei was tested. PI counterstaining of the cells allowed definitive localization of cell nuclei, and overlay of the anti-IgG and PI fluorescent images confirmed nuclear localization by 3E10, 5C5, and 5C6. To confirm that 5C6 penetrates into cell nuclei DLD1 colon cancer cells were treated with control media or media containing 5C6. PI counterstaining allowed direct visualization of cell nuclei, and overlay of anti-IgG and PI fluorescent images confirmed nuclear localization by 5C6 in the DLD1 cells.

Example 2

5C6 Induces γH2AX in BRCA2—Cancer Cells

Materials and Methods
γH2AX Assays
BRCA2$^{(+)}$ and BRCA2$^{(-)}$ DLD1 cells were treated with control media or media containing 10 μM 3E10, 5C5, or 5C6 for one hour, followed by evaluation of the percentage of cells positive for γH2AX (a marker of DNA double strand breaks) by immunofluorescence. Cells were washed with PBS, fixed with chilled 100% ethanol for 5 minutes, washed again with PBS, blocked with 1% BSA/PBS for 45 minutes and then probed with Alexa488-conjugated anti-γH2AX antibody overnight at 4° C. (Cell Signaling). Fluorescent signal corresponding to γH2AX (a marker of DNA double-strand breaks) was then imaged using an EVOS fl digital fluorescence microscope using a GFP filter.

Results
The antibodies were screened for the ability to induce DNA double-strand breaks in the DLD1 cells. None of the antibodies induced γH2AX in the BRCA2$^{(+)}$ cells. Similarly, neither 3E10 nor 5C5 caused any significant increase in the percentage of γH2AX-positive BRCA2$^{(-)}$ cells. 5C6, however, caused an increase in the percentage of γH2AX-positive BRCA2$^{(-)}$ cells to 10.3%±2.2 compared to 2.3%±0.7 in the control cells (p=0.01) (FIG. 1). The observed increase in percentage of γH2AX-positive BRCA2$^{(-)}$ cells demonstrated that the live cells in culture were responding to DNA damage induced by 5C6.

Example 3

5C6 Catalyzes Degradation of Single-Stranded DNA

Materials and Methods
Catalytic Assays—Single-Stranded Plasmid DNA Assays
Single-stranded M13mp18 DNA (New England Biolabs, Ipswich, Mass.) was incubated with 0-2.5 μM 5C6 for 0-60 minutes in binding buffer (50 mM Tris-HCl, 100 mM NaCl, 10 mM MgCl$_2$). The reaction was terminated by the addition of 1% SDS. Samples were boiled and then run on 1% agarose gels and stained with SYBR Gold (Life Technologies) for 30 minutes. The proportion of DNA remaining after treatment relative to untreated M13mp18 DNA was then calculated by band densitometry using Image J (National Institutes of Health, Bethesda, Mass.). Single-stranded M13mp18 circular DNA was incubated with buffer containing 2.5 μM 5C6 for 0-60 minutes, followed by visualization of DNA on an agarose gel.

The percentage of M13mp18 DNA remaining after incubation with 5C6 was quantified relative to untreated M13mp18 DNA. 5C6 degrades single-stranded DNA in a dose-dependent manner. M13mp18 DNA was incubated with buffer containing 0-2.5 μM 5C6 for 10 minutes, followed by visualization on an agarose gel. The percentage of M13mp18 DNA remaining after incubation with 5C6 was quantified relative to untreated M13mp18 DNA.

Figures 2A, 2B, 2C:
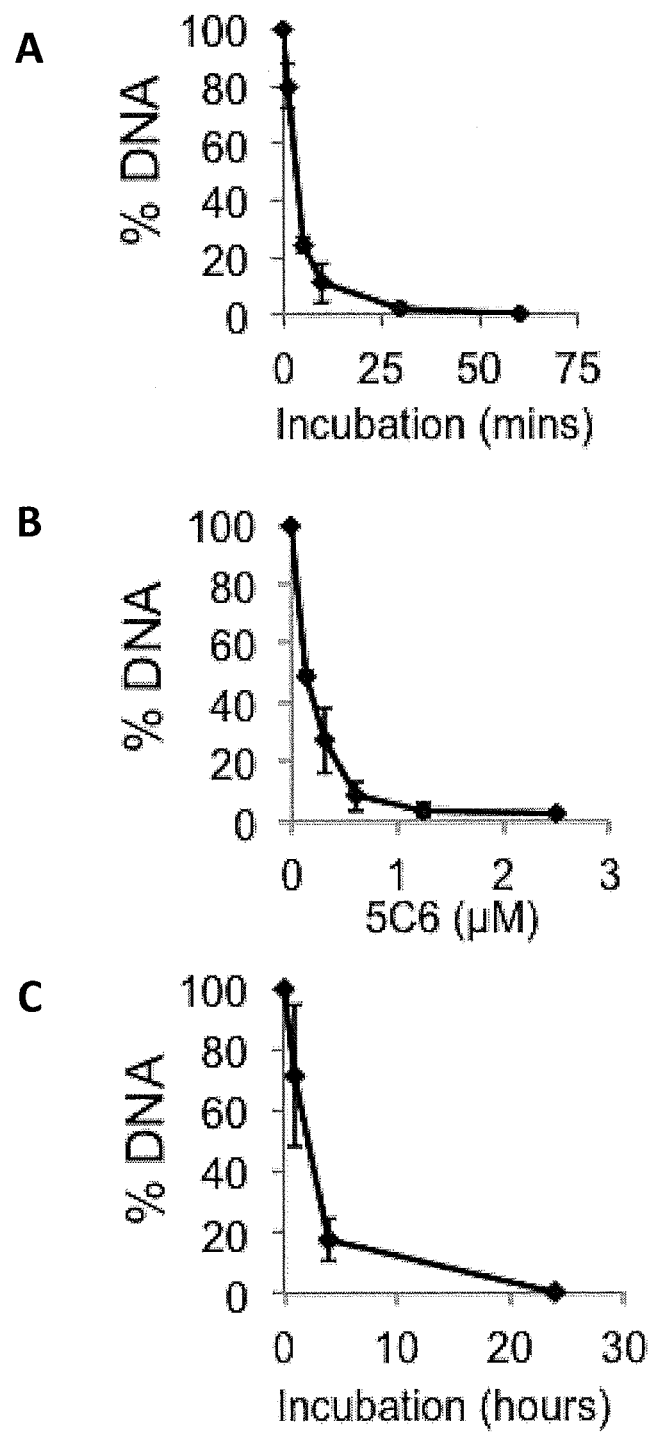
FIGS. 2A-2C are line graphs.

Statistics
P values were determined by paired Student's t-test.
Results
Based on the results of the γH2AX assay, 5C6 was selected for further study, to verify that it has nucleolytic activity in vitro. M13mp18 single-stranded DNA was incubated with control buffer or 2.5 μM 5C6 for 0-60 minutes, followed by visualization of DNA on an agarose gel. 5C6 catalyzed degradation of the single-stranded DNA in a time-dependent manner (FIG. 2A). Next, M13mp18 single stranded DNA was incubated with control buffer or 0-2.5 μM 5C6 for 10 minutes followed by visualization of DNA on an agarose gel, and 5C6 was observed to catalyze degradation of the single-stranded DNA in a dose-dependent manner (FIG. 2B).

Example 4

5C6 Catalyzes Degradation of Double-Stranded Plasmid DNA

Materials and Methods
Double-Stranded Plasmid DNA Assays
pBluescript (Agilent Technologies, Englewood, Colo.) was used in double-stranded plasmid DNA assays by incubating with 6.6 μM 5C6 for 0-24 hours in binding buffer at 37° C. Samples were then boiled, and DNA conformations were visualized on 1% agarose gels with ethidium bromide. The proportion of DNA remaining after treatment relative to untreated pBluescript DNA was then calculated by band densitometry using Image J.

Results
The effect of 5C6 on double-stranded plasmid DNA was examined by incubating the antibody with double-stranded plasmid DNA (pBluescript) and evaluating its effect on the plasmid by visualization on an agarose gel. 5C6 catalyzed a time-dependent degradation of the plasmid DNA (FIG. 2C). Of note, at the early time points 5C6 also appeared to first catalyze an increase in proportion of plasmid in the relaxed, nicked conformation (N) relative to supercoiled (S), followed by near complete plasmid degradation by time 24 hours (FIG. 2C). This demonstrated that 5C6 causes DNA single-strand breaks that first lead to plasmid relaxation followed then by complete plasmid degradation as additional strand breaks accumulate. Taken together, the observations that 5C6 degrades both single-stranded and double-stranded plasmid DNA confirm that it is a nucleolytic lupus autoantibody.

Example 5

5C6 has a Differential Effect on the Growth of BRCA2$^{(+)}$ and BRCA2$^{(-)}$ Cells Materials and Methods
Cell Growth Assays
BRCA2$^{(+)}$ and BRCA2$^{(-)}$ DLD1 cells were plated in 48 well plates at 1×10$^4$ and allowed to adhere overnight. The cells were then treated with control media or media containing 10 μM 5C6 for 1 hour. Cells were then washed, fixed, and probed for the presence of γH2AX with an Alexa-488 conjugated antibody. Light and immunofluorescence images were observed. The percentage of γH2AX-positive BRCA2$^{(-)}$ cells after treatment with control or 5C6 was quantified.

Results

To confirm that 5C6 is more toxic to BRCA2$^{(-)}$ than BRCA2$^{(+)}$ cells, the effect of 5C6 on the proliferation of BRCA2$^{(+)}$ and BRCA2$^{(-)}$ DLD1 cells growing as sub-confluent monolayers was assessed. BRCA2$^{(+)}$ and BRCA2$^{(-)}$ DLD1 cells were treated with control media or media containing 10 μM 5C6. Four days later total viable cell counts were recorded. 5C6 did not significantly inhibit the growth of the BRCA2$^{(+)}$ cells (percent growth inhibition of 2.8%±9). However, 5C6 significantly impaired the growth of the BRCA2$^{(-)}$ cells (percent growth inhibition of 41% 18). 5C6 is toxic to BRCA2$^{(-)}$ DLD1 cells.

Figures 3A, 3B:
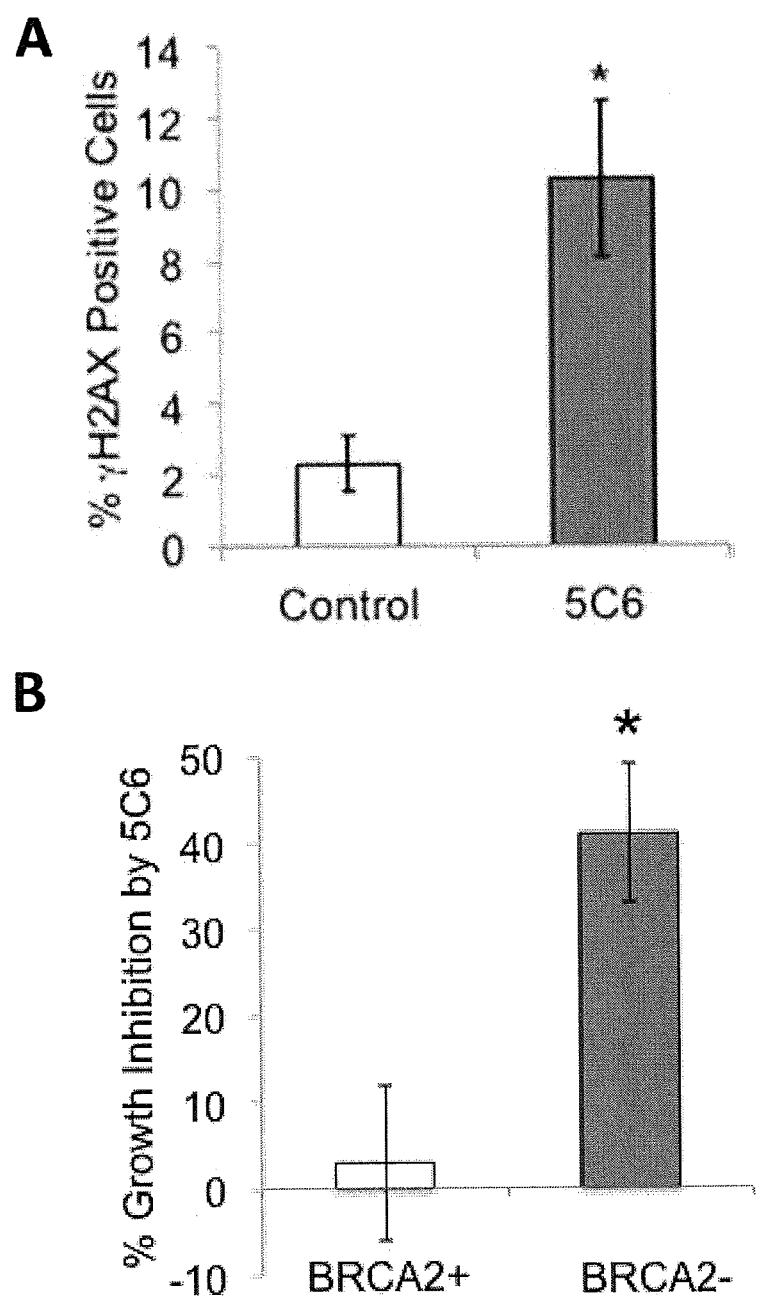
FIGS. 3A and 3B are bar graphs.
Figure 4A:
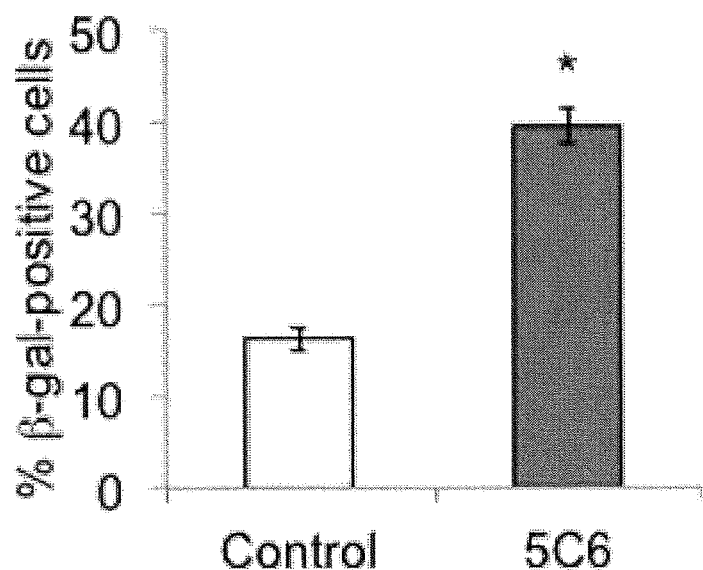
FIG. 4A is a bar graph showing % β-gal-positive cells as a marker of senescence for BRCA2-DLD1 cells treated with control media (control) or media containing 6.6 μM antibody 5C6 (5C6), respectively. *p=0.009.
Figure 4B:
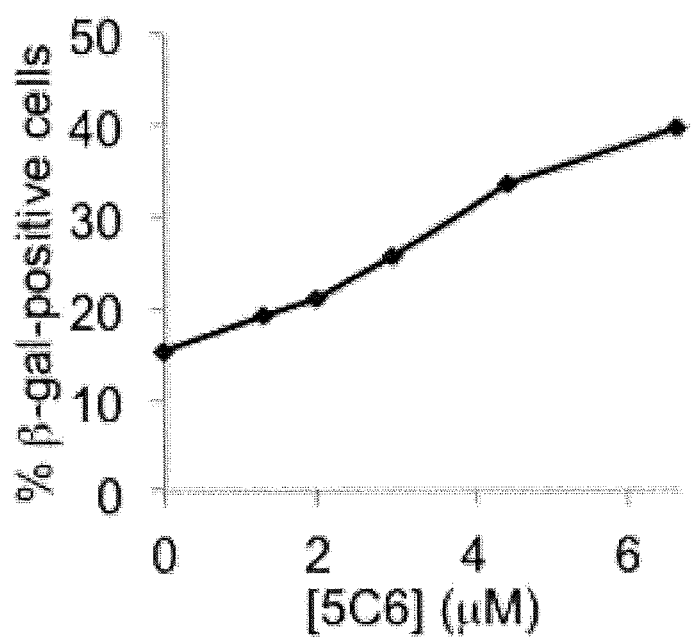
FIG. 4B is a graph showing % β-gal-positive cells as a marker of senescence for BRCA2-DLD1 cells treated with an increasing concentration of antibody 5C6 (0-6 μM).

5C6 increased the percentage of γH2AX-positive cells ~5-fold relative to control media. These results are consistent with the finding that 5C6 selectively induced an increase in γH2AX in BRCA2$^{(-)}$ cells and demonstrate that 5C6 is significantly more toxic to BRCA2$^{(-)}$ than BRCA2$^{(+)}$ cells (FIG. 3A).

Example 6

5C6 has a Differential Effect on the Clonogenic Survival of BRCA2+ and BRCA2− Cells Materials and Methods
Clonogenic Survival Assays Surviving fractions of BRCA2$^{(+)}$ and BRCA2$^{(-)}$ DLD1 cells were treated with control media or media containing 10 μM 5C6 for 4 days. Cells were then harvested and counted using trypan blue. Percent growth inhibition by 5C6 was then calculated by comparing the total number of viable cells treated with 5C6 relative to cells treated with control, as previously described (Hansen, et al., *Science Translational Medicine*, 4:157ra142 (2012)).

Results

The effect of 5C6 on the clonogenic survival of BRCA2$^{(+)}$ and BRCA2$^{(-)}$ DLD1 cells was tested using a colony formation assay. 5C6 reduced the surviving fraction of the BRCA2$^{(+)}$ cells to 0.66±0.06, which is consistent with a previous report on the toxicity of a catalytic lupus antibody on cells (Lee, et al., *Bioorg. Med. Chem.* 15:2016-2023 (2007)). 5C6 had a significantly greater effect on the BRCA2$^{(-)}$ cells, with surviving fraction reduced to 0.36±0.07 (p<0.02) (FIG. 3B). These results further demonstrate that 5C6 is more toxic to BRCA2$^{(-)}$ than BRCA2$^{(+)}$ cells.

These studies demonstrate that the nucleolytic lupus autoantibodies should be useful as targeted therapies for DNA repair-deficient malignancies. A wide range of human malignancies harbor deficiencies in DNA repair (Hoeijmakers, *N. Engl. J. Med.*, 361:1475-1485 (2009)), and this therapeutic strategy therefore has potential for applications in the treatment of numerous tumors.

These findings demonstrate the potential utility of 5C6 in targeted therapy for DNA repair-deficient malignancies and strengthen the rationale for studies of additional lupus autoantibodies in order to identify the best candidates for development as therapeutic agents. In addition, the toxic effect of 5C6 on BRCA2 deficient cells provides further support for the hypothesis that some lupus autoantibodies contribute to the unusual cancer risk profile associated with systemic lupus erythematosus.

Example 7

5C6 Induces Senescence in the BRCA2-Deficient DLD1 Cells

Materials and Methods
Propidium Iodide Uptake

BRCA2$^{(-)}$ DLD1 cells were plated in 96 well plates at 3×10$^4$ and allowed to adhere overnight. The cells were then treated with control media or media containing 10 μM 5C6 overnight at 37° C. Antibody was then removed and cells were stained with 1 μg/ml PI for 15 minutes at room temperature. Cells were then imaged for PI uptake using an EVOS fl digital fluorescence microscope using an RFP filter. Cell membrane integrity was examined by visualization of PI uptake.

Cellular Senescence Assay

BRCA2-DLD1 cells were plated in 12 well plates at 2×10$^4$ and allowed adhere overnight. The cells were then treated with media containing 0-6.6 μM 5C6. Cells were incubated at 37° C. for 4 days. The Senescence-βGal Staining Kit (Cell Signaling Technology) was used for β-gal staining. After treatment cells were washed, fixed and stained for the presence of β-gal at pH 6.0. Cells were then imaged (Olympus IX70, Tokyo, Japan) and percentage of β-gal positive cells calculated.

Results

To investigate the mechanism by which 5C6 suppresses the growth of BRCA2-DLD1 cells the effect of 5C6 on membrane integrity was examined as a marker for apoptosis or necrosis. BRCA2$^{(-)}$ DLD1 cells were treated with control or 10 μM 5C6 and then treated with propidium iodide (PI).

5C6 did not appear to induce apoptosis or necrosis of BRCA2$^{(-)}$ DLD1 cells. No significant increase in the percentage of PI-positive cells in the presence of 5C6 relative to control media was observed, which suggested that neither apoptosis nor necrosis are the primary mechanisms responsible for the effect of 5C6 on BRCA2− cells. The effect of 5C6 on induction of cell senescence was tested by examining the relative expression of β-galactosidase (β-gal) in cells treated with 5C6. As shown in FIGS. 4A and 4B, 5C6 yielded a significant increase in β-gal expression in the BRCA2-DLD1 cells, which suggests that 5C6 suppresses the growth of the cells by inducing senescence. Specifically, the impact of 5C6 on the percentage of β-gal-positive cells was dose dependent. At a dose of 6.6 μM 5C6 increased the percentage of n-gal-positive cells to 39.3%±1.8 compared to 16.3%±1.3 in cells treated with control media.

Together, these data demonstrate that 5C6 induces γH2AX in BRCA2$^{(-)}$ but not BRCA2$^{(+)}$ cells and selectively suppresses the growth of the BRCA2$^{(-)}$ cells. Mechanistically, 5C6 appears to induce senescence in the BRCA2$^{(-)}$ cells. Senescence is a well-known response to DNA damage, and DNA damaging agents, including many chemotherapeutics, induce senescence after prolonged exposure (Sliwinska, et al., *Mech. Ageing Dev.*, 130:24-32 (2009); to Poele, et al., *Cancer Res.* 62:1876-1883 (2002); Achuthan, et al., *J. Biol. Chem.*, 286:37813-37829 (2011)).

These observations establish that 5C6 penetrates cell nuclei and damages DNA, and that cells with preexisting defects in DNA repair due to BRCA2 deficiency are more sensitive to this damage than cells with intact DNA repair.

Unless defined otherwise, all technical and scientific terms used herein have the same meanings as commonly understood by one of skill in the art to which the described invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A pharmaceutical composition comprising
a) a cell-penetrating, nucleolytic antibody, or antigen binding fragment thereof, comprising:
a heavy chain variable region comprising respectively the first, second, and third complementarity determining regions (CDRs) of SEQ ID NO:5 or humanized variants thereof, and
a light chain variable region comprising respectively the first, second, and third CDRs of SEQ ID NO:1 or humanized variants thereof,
in a unit dosage between about 0.01 and about 100 mg/kg body weight of a human; and
b) a pharmaceutically acceptable excipient for injection.

2. The pharmaceutical composition of claim 1, further comprising one or more antineoplastic or radio-sensitizing agents selected from the group consisting of cisplatin, cytoxan, doxorubicin, methotrexate, mitomycin c, nitrogen mustard, hydroxyurea, bevacizumab, cetuximab, rituximab, trastuzumab, tirapazamine, temozolomide, camptothecin, cisplatin, gemcitabine, 5-fluorouracil, hydroxyurea, pentoxifylline, vinorelbine, and combinations thereof.

3. The pharmaceutical composition of claim 1, in the unit dosage form for intravenous injection or intratumoral injection.

4. The pharmaceutical composition of claim 1, wherein the antibody or antigen binding fragment thereof, is a monovalent or multivalent single chain variable fragment (scFv).

5. The pharmaceutical composition of claim 1, wherein
the first light chain CDR comprises the amino acid sequence of SEQ ID NO:2;
the second light chain CDR comprises the amino acid sequence of SEQ ID NO:3;
the third light chain CDR comprises the amino acid sequence of SEQ ID NO:4;
the first heavy chain CDR comprises the amino acid sequence of SEQ ID NO:6;
the second heavy chain CDR comprises the amino acid sequence of SEQ ID NO:7; and
the third heavy chain CDR comprises the amino acid sequence of SEQ ID NO:8.

6. The pharmaceutical composition of claim 1, wherein the light chain variable region comprises the amino acid sequence of SEQ ID NO:1 and the heavy chain variable region comprises the amino acid sequence of SEQ ID NO:5.

7. The pharmaceutical composition of claim 1, wherein the antibody or antigen binding fragment thereof, is a humanized antibody or an antigen binding fragment thereof.

8. The pharmaceutical composition of claim 7, wherein
the first light chain CDR comprises the amino acid sequence of SEQ ID NO:2;
the second light chain CDR comprises the amino acid sequence of SEQ ID NO:3;
the third light chain CDR comprises the amino acid sequence of SEQ ID NO:4;
the first heavy chain CDR comprises the amino acid sequence of SEQ ID NO:6;
the second heavy chain CDR comprises the amino acid sequence of SEQ ID NO:7; and
the third heavy chain CDR comprises the amino acid sequence of SEQ ID NO:8.

9. The pharmaceutical composition of claim 1, wherein the antibody or antigen binding fragment thereof, is a chimeric antibody.

10. The pharmaceutical composition of claim 9, wherein
the first light chain CDR comprises the amino acid sequence of SEQ ID NO:2;
the second light chain CDR comprises the amino acid sequence of SEQ ID NO:3;
the third light chain CDR comprises the amino acid sequence of SEQ ID NO:4;
the first heavy chain CDR comprises the amino acid sequence of SEQ ID NO:6;
the second heavy chain CDR comprises the amino acid sequence of SEQ ID NO:7; and
the third heavy chain CDR comprises the amino acid sequence of SEQ ID NO:8.

11. The pharmaceutical composition of claim 10, wherein the light chain variable region comprises the amino acid sequence of SEQ ID NO:1 and the heavy chain variable region comprises the amino acid sequence of SEQ ID NO:5.

12. The pharmaceutical composition of claim 1, wherein the antibody or antigen binding fragment thereof, is not an IgG2a-k mouse monoclonal antibody.

* * * * *

SEQUENCE LISTING

```
<160> NUMBER OF SEQ ID NOS: 15

<210> SEQ ID NO 1
<211> LENGTH: 112
<212> TYPE: PRT
<213> ORGANISM: Mus musculus

<400> SEQUENCE: 1

Asp Ile Val Leu Thr Gln Ser Pro Ala Ser Leu Ala Ala Val Ser Leu
1               5                   10                  15

Gly Glu Arg Ala Thr Ile Ser Tyr Arg Ala Ser Lys Ser Val Ser Thr
            20                  25                  30

Ser Gly Tyr Ser Tyr Met His Trp Asn Gln Gln Lys Pro Gly Gln Ala
        35                  40                  45

Pro Arg Leu Leu Ile Tyr Leu Val Ser Asn Leu Glu Ser Gly Val Pro
    50                  55                  60

Ala Arg Phe Ser Gly Ser Gly Ser Gly Thr Asp Phe Thr Leu Asn Ile
65                  70                  75                  80

His Pro Val Glu Glu Glu Asp Ala Ala Thr Tyr Tyr Cys Gln His Ile
                85                  90                  95

Arg Glu Leu Asp Thr Phe Phe Gly Gly Thr Lys Leu Glu Ile Lys
            100                 105                 110

<210> SEQ ID NO 2
<211> LENGTH: 15
<212> TYPE: PRT
<213> ORGANISM: Mus musculus

<400> SEQUENCE: 2

Arg Ala Ser Lys Ser Val Ser Thr Ser Gly Tyr Ser Tyr Met His
1               5                   10                  15

<210> SEQ ID NO 3
<211> LENGTH: 7
<212> TYPE: PRT
<213> ORGANISM: Mus musculus

<400> SEQUENCE: 3

Leu Val Ser Asn Leu Glu Ser
1               5

<210> SEQ ID NO 4
<211> LENGTH: 9
<212> TYPE: PRT
<213> ORGANISM: Mus musculus

<400> SEQUENCE: 4

Gln His Ile Arg Glu Leu Asp Thr Phe
1               5

<210> SEQ ID NO 5
<211> LENGTH: 120
<212> TYPE: PRT
<213> ORGANISM: Mus musculus

<400> SEQUENCE: 5
```

```
Gln Leu Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Ala Lys Arg Leu Glu Trp Val
        35                  40                  45

Ala Thr Ile Ser Ser Gly Gly Gly Ser Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Arg Ala Tyr Ser Lys Arg Gly Ala Met Asp Tyr Trp Gly Gln
            100                 105                 110

Gly Thr Ser Val Thr Val Ser Ser
        115                 120

<210> SEQ ID NO 6
<211> LENGTH: 5
<212> TYPE: PRT
<213> ORGANISM: Mus musculus

<400> SEQUENCE: 6

Ser Tyr Thr Met Ser
1               5

<210> SEQ ID NO 7
<211> LENGTH: 17
<212> TYPE: PRT
<213> ORGANISM: Mus musculus

<400> SEQUENCE: 7

Thr Ile Ser Ser Gly Gly Gly Ser Thr Tyr Tyr Pro Asp Ser Val Lys
1               5                   10                  15

Gly

<210> SEQ ID NO 8
<211> LENGTH: 11
<212> TYPE: PRT
<213> ORGANISM: Mus musculus

<400> SEQUENCE: 8

Arg Ala Tyr Ser Lys Arg Gly Ala Met Asp Tyr
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Artificial Protein linker

<400> SEQUENCE: 9

Gly Gln Ser Ser Arg Ser Ser
1               5

<210> SEQ ID NO 10
<211> LENGTH: 18
<212> TYPE: PRT
<213> ORGANISM: Artificial Sequence
<220> FEATURE:
```

```
<223> OTHER INFORMATION: Artificial protein linker

<400> SEQUENCE: 10

Gly Gln Ser Ser Arg Ser Ser Gly Gly Ser Gly Gly Gly
1               5                   10                  15

Gly Ser

<210> SEQ ID NO 11
<211> LENGTH: 6
<212> TYPE: PRT
<213> ORGANISM: Artificial Sequence
<220> FEATURE:
<223> OTHER INFORMATION: Artificial Protein Linker

<400> SEQUENCE: 11

Gly Ser Gly Ser Gly Ser
1               5

<210> SEQ ID NO 12
<211> LENGTH: 6
<212> TYPE: PRT
<213> ORGANISM: Artificial Sequence
<220> FEATURE:
<223> OTHER INFORMATION: Artificial Protein Linker

<400> SEQUENCE: 12

Ala Ser Gly Gly Gly Ser
1               5

<210> SEQ ID NO 13
<211> LENGTH: 15
<212> TYPE: PRT
<213> ORGANISM: Artificial Sequence
<220> FEATURE:
<223> OTHER INFORMATION: Artificial Protein Linker

<400> SEQUENCE: 13

Gly Gly Gly Gly Ser Gly Gly Gly Ser Gly Gly Gly Gly Ser
1               5                   10                  15

<210> SEQ ID NO 14
<211> LENGTH: 20
<212> TYPE: PRT
<213> ORGANISM: Artificial Sequence
<220> FEATURE:
<223> OTHER INFORMATION: Artificial Protein Linker

<400> SEQUENCE: 14

Gly Gly Gly Gly Ser Gly Gly Gly Gly Ser Gly Gly Gly Gly Ser Gly
1               5                   10                  15

Gly Gly Gly Ser
            20

<210> SEQ ID NO 15
<211> LENGTH: 18
<212> TYPE: PRT
<213> ORGANISM: Artificial Sequence
<220> FEATURE:
<223> OTHER INFORMATION: Artificial Protein Linker

<400> SEQUENCE: 15

Gly Gly Ser Ser Arg Ser Ser Ser Gly Gly Gly Gly Ser Gly Gly
1               5                   10                  15

Gly Gly
```